US 7,208,466 B1

(12) United States Patent
Foster et al.

(10) Patent No.: US 7,208,466 B1
(45) Date of Patent: Apr. 24, 2007

(54) USE OF A LECTIN OR CONJUGATES FOR MODULATION OF C-FIBRE ACTIVITY

(75) Inventors: Keith Alan Foster, Salisbury (GB); John Andrew Chaddock, Salisbury (GB); Conrad Padraig Quinn, Lilburn, GA (US)

(73) Assignee: The Health Protection Agency (GB)

( * ) Notice: Subject to any disclaimer, the term of this patent is extended or adjusted under 35 U.S.C. 154(b) by 0 days.

(21) Appl. No.: 09/937,484

(22) PCT Filed: Mar. 31, 2000

(86) PCT No.: PCT/GB00/01247

§ 371 (c)(1),
(2), (4) Date: Jan. 23, 2002

(87) PCT Pub. No.: WO00/57897

PCT Pub. Date: Oct. 5, 2000

(30) Foreign Application Priority Data

Mar. 31, 1999 (GB) ................................. 9907429.6

(51) Int. Cl.
 *A61K 38/00* (2006.01)
 *A61K 51/00* (2006.01)
 *A61M 36/14* (2006.01)
 *C07K 16/00* (2006.01)
 *C07K 17/00* (2006.01)

(52) U.S. Cl. ........................... 514/2; 424/1.69; 530/325
(58) Field of Classification Search .................... 514/8, 514/2
See application file for complete search history.

(56) References Cited

U.S. PATENT DOCUMENTS

| 5,239,062 A | 8/1993 | Blattler et al. |
| 5,242,687 A | 9/1993 | Tykocinski et al. |
| 5,433,946 A | 7/1995 | Allen, Jr. et al. ........... 424/94.3 |
| 5,668,255 A | 9/1997 | Murphy |
| 5,721,207 A | 2/1998 | Noble et al. |
| 5,989,545 A | 11/1999 | Foster et al. |
| 6,235,313 B1 * | 5/2001 | Mathiowitz et al. ......... 424/486 |
| 2002/0137674 A1 * | 9/2002 | Oldham et al. ................. 514/8 |

FOREIGN PATENT DOCUMENTS

| DE | 197 35 105 A1 | 3/1999 |
| EP | 0 602 686 A2 | 6/1994 |
| WO | WO 92/15327 | 9/1992 |
| WO | WO 93/04191 | 3/1993 |
| WO | WO 93/15766 | 8/1993 |
| WO | WO 94/21300 | 9/1994 |
| WO | WO 94/28923 | 12/1994 |
| WO | WO 95/32738 | 12/1995 |
| WO | WO 96/12802 | 5/1996 |
| WO | WO 96/33273 | 10/1996 |
| WO | WO 97/18790 | 5/1997 |
| WO | WO 98/07864 | 2/1998 |
| WO | WO 98/08540 | 3/1998 |
| WO | WO 99/17806 | 4/1999 |
| WO | WO 91/09871 | 7/1999 |

OTHER PUBLICATIONS

Arango, R., et al., "Cloning and sequence analysis of the *Erythrina cerallodendron* lectin cDNA," *FEBS Lett.* 264: 109-111, Elsevier Science (1990).
Arango, P., et al., "Expression of *Erythrina corallodendron* lectin in *Escherichia coli*," *Eur. J. Biochem.* 205:575-581, Blackwell Science Ltd. (1992).
Diaz, A. and Dickenson, A.H., "Blockade of spinal N- and P-type, but not L-type, calcium channels inhibits the excitability of rat dorsal horn neurones produced by subcutaneous formalin inflammation," *Pain* 69:93-100, Elsevier Science Ireland Ltd. (1997).
Edmonds, B.T. and Koenig, E., "Transmembrane Cytoskeletal Modulation in Preterminal Growing Axons: I. Arrest of Balk and Organello Transport in Goldfish Retinal Ganglion Cell Axons Regenerating in Vitro by Lectins Binding to Sialoglycoconjugates," *Cell Motil. Cytoskeleton* 17:106-117, Wiley-Liss, Inc. (1990).
Edmonds, B.T. and Koenig, E., "Transmembrane cytoskeletal modulation in preterminal growing axons. II. *Limax flavus* agglutinin-induced receptor redistribution, capping and internalization in varicosities of growing axons," *J. Neurocytology* 20:232-247, Chapman and Hall Ltd. (1991).

(Continued)

*Primary Examiner*—Cecilia J. Tsang
*Assistant Examiner*—Maury Audet
(74) *Attorney, Agent, or Firm*—Sterne, Kessler, Goldstein & Fox P.L.L.C.

(57) ABSTRACT

The present invention relates to the treatment of pain and to compounds that modulate C-fibre activity. In particular, the present invention relates to the use of a lectin in the manufacture of a medicament for modulation of C-fibre neuron activity, and to lectin conjugates. The lectin conjugates comprise a lectin coupled to a peptide or protein, wherein the peptide or protein is substantially free of Clostridial neurotoxin enzyme activity. The present invention also concerns methods for manufacturing conjugates. The compounds and compositions described have particular application in the treatment of diseases of which C-fibre activity is a component. Such diseases include pain, inflamation, psoriasis and other C-fibre related conditions.

4 Claims, 14 Drawing Sheets

OTHER PUBLICATIONS

Garber, N., et al., "On the specificity of the : -galactose-binding lectin (PA-I) of *Pseudomonas acruginosa* and its strong binding to hydrophobic derivatives ot :- galactose and thiocalactose," *Biochem. Biophys. Acta 1116*:331-333, Elsevier Science (1992).

Garret, C., et al., "Pharmacological properties of a potent and selective nonpeptide substance P antagonist," *Proc. Natl. Acad. Sci. (USA) 68*:10208-10212, National Academy of Sciences (1991).

Gupta, D., et al., "Differences in the Cross-Linking Activities of Native and Recombinant *Erythrina corallodendron* Lectin with Asialofetuin. Evidence for Carbohydrate-Carbohydrate Interactions in Lectin-Glycoprotein Complexes," *Biochemistry 33*:2503-2508, American Chemical Society (1994).

Heilman, R.D., et al., "An Evaluation of the Hot Plate Technique to Study Narcotic Antagonists," *Res. Comm. Chem. Path. Pharm. 13*:635-647, PJD Publications Ltd. (1976).

Iglesias, J.L., et al., "Purification and Properties of a O-Galactose/ N-Acetyl galactosamine-Specific Lectin from *Erythrina cristagalli,*" *Eur. J. Biochem. 123*:247-252, Blackwell Science Ltd. (1982).

Lembeck, F. and Holzer, P., "Substance P as Neurogenic Mediator of Antidromic Vasodilation and Neurogenic Plasma Extravasation," *Naunyn-Schmiedeberg's Arch. Pharmacol. 318*:175-183, Springer-Verlag (1979).

Printer, E., et al., "Lack of the evidence for tachykin:n NK$_2$ receptor-mediated neutrophil accumulation in the rat cutaneous microvasculature by thermal injury," *Eur. J. Phamacol. 369*:91-98, Elsevier Science (Mar. 1999).

Shone, C.C., et al., "A 50-kDo fragment from the NH-terminus of the heavy substrate of *Clostridium botulinum* type A neurotoxin forms channels in lipid vesicles," *Eur. J. Biochem. 167*:175-180, Blackwell Science Ltd. (1987).

Silverman, J.D. and Kruger, L., "Selective neuronal glycoconjugate expression in sensory and autonomic ganglia: relation of lectin reactivity to peptide and enzyme markers," *J. Neurocytology 19*:789-801, Chapman and Hall Ltd. (1990).

Streit, W.J., et al., "Histochemical Localization of Calactose-Containing Glycoconjugate in Sensory Neurons and Their Processes in the Central and Peripheral Nervous System of the Rat," *J. Histochem. Cytochem. 33*:1042-1052, The Histochemical Society, Inc. (1985).

Welch, K. and Foster, K., "Chapter 26- Cell Culture of Neurons of the Peripheral Nervous System of Birds and Mammals: 26.1.1 Embryonic Rat Spinal Sensory Ganglia," in *The Neuron in Tissue Culture*, Haynes, L.W., ed., John Wiley & Sons Ltd., New York, N.Y., pp. 389-393 (Dec. 1999).

Zhou, L., et al., "Expression and Purification of the Light Chain of Botulinum Neurotoxin A: A Single Mutation Abolishes Its Cleavage of SNAP 25 and Neurotoxicity after Reconstitution with the Heavy Chain," *Biochemistry 34*:15175-15181, American Chemical Society (1995).

English Abstract of European Patent No. EP 0 602 686 A2 from esp@cones database -12.

Bizzini, B., "Investigation of the Mode of Action of Tetanus Toxin With the Aid of Hybrid Molecules Consisting in Part of Tetanus Toxin-Derived Fragments," in *Bacterial Protein Toxins,* Academic Press London, pp. 427-434 (1984).

Adar, R., et. al., "The amino acid sequence of *Erythrina corallodendron* lectin and its homology with other legume lectins," *FEBS Lett. 257*:81-85, Elsevier Science B.V. (1989).

Arora, N., et. al., "Cytotoxic Effects of a Chimeric Protein Consisting of Tetanus Toxin Light Chain and Anthrax Toxin Lethal Factor in Non-neuronal Cells," *J. Biol. Chem. 269*:26165-26171, American Society for Biochemistry and Molecular Biology (1994).

Brinkmann, U., et. al., "A recombinant immunotoxin containing a disulfide-stabilized Fv fragment," *Proc. Natl. Acad. Sci. USA 90*:7538-7542, Abstract No. 8356052, National Academy of Sciences (1993).

Kurazono, H., et. al., "Minimal Essential Domains Specifying Toxicity of the Light Chains of Tetanus Toxin and Botulinum Neurotoxin Type A," *J. Biol. Chem. 267*:14721-14729, The American Society for Biochemistry and Molecular Biology, Inc. (1992).

Lamb, F. I., et. al., "Nucleotide sequence of cloned cDNA coding for preproricin," *Eur. J. Biochem. 148*:265-270, Blackwell Science Ltd. on behalf of the Federation of European Biochemical Societies, (1985).

Law, I. J., "Cloning and expression of cDNA for galactose-binding lectin from peanut nodules," *Plant Science 115*:71-79, Elsevier Science Ireland Ltd. (1996).

Lorberboum-Galski, H., et. al., "Cytotoxic activity of an interleukin 2-*Pseudomonas* exotoxin chimeric protein produced in *Escherichia coli,*" *Proc. Natl. Acad. Sci. USA 85*:1922-1926, National Academy of Sciences (1988).

Murphy, J.R., "Diphtheria-related peptide hormone gene fusions: a molecular genetic approach to chimeric toxin development," *Cancer Treat. Res. 37*:123-140, Kluwer Academic (1988).

"NeuroBloc (Botulinum Toxin Type B) For Cervical Dystonia Launched in UK," *Doctor's Guide*, P/S/L Consulting Group Inc. (Mar. 2001), visited Nov. 28, 2001 at <http://ww.pslgroup.com/dg/1F4216.htm>.

O'Hare, M., et. al., "Cytotoxicity of a recombinant ricin-A-chain fusion protein containing a proteolytically-cleavable spacer sequence," *FEBS Lett. 273*:200-204. Elsevier Science B.V. (1990).

Plank, C., et. al., "The influence of Endosome-disruptive Peptides on Gene Transfer Using Synthetic Virus-like Gene Transfer Systems," *J. Biol. Chem. 269*:12918-12924, American Society for Biochemistry and Molecular Biology (1994).

Van Damme, E.J., et. al., "Molecular cloning of the bark and seed lectins from the Japanese pagoda tree (*Saphora japonica*)," *Plant Molec. Biol. 33*:523-536, Kluwer Academic Publishers (1997).

Williams, D.P., et. al., "Diphtheria toxin receptor binding domain substitution with interleukin-2: genetic construction and properties of a diptheria toxin-related interleukin-2 fusion protein," *Protein Eng. 1*:493-498, Oxford University Press (1987).

Wood, K.A., et. al., "Preproabin: genomic cloning, characterisation and the expression of the A-chain in *Escherichia coli,*" *Eur. J. Biochem. 198*:723-732, Blackwell Science Ltd. on behalf of the Federation of European Biochemical Societies, (1991).

Yamaguchi, O., et. al., "Chemical Structures of Two Subunits, A-Subunit and B-Subunit, of Galactose-Specific Isolectins from *Erythrina variegata* Seeds," *J. Biochem. (Tokyo) 114*:560-566, Oxford University Press for Japanese Biochemical Society (1993).

Black, J.D., and Dolly, J.O., "Interaction of $^{125}$I-Labeled Botulinum Neurotoxins with Nerve Terminals. I. Ultrastructural Autoradiographic Localization and Quantitation of Distinct Membrane Acceptors for Types A and B on Motor Nerves," *J. Cell Biol. 103*:521-534, The Rockefeller University Press (1986).

Blaustein, R.O., et. al., "The N-terminal half of the heavy chain of botulinum type A neurotoxin forms channels in planar phospholipid bilayers," *FEBS Letts. 226*:115-120, Elsevier Science Publishers B.V. (1987).

Shone, C.C., et. al., "Inactivation of *Clostridium botulinum* type A neurotoxin by trypsin and purification of two tryptic fragments: Proteolytic action near the COOH-terminus of the heavy subunit destroys toxin-binding activity," *Eur. J. Biochem. 151*:75-82, Springer International (1985).

Sutton, J.M., et. al., "Tyrosine-1290 of tetanus neurotoxin plays a key role in its binding to gangliosides and functional binding to neurones," *FEBS Letts. 493*:45-49, Elsevier Science B.V. (Mar. 2001).

Yamazaki, N., et. al., "Endogenous lectins as targets for drug delivery," Advanced *Drug Delivery Reviews 43*:225-244, Elsevier Science B.V. (Sep. 2000).

Dialog File 351, WPI Accession No. 1999-168079/199915, Derwent WPI English language abstract for DE 197 35 105 (Document AO2).

Welch, M.J., et. al., "Sensitivity of embryonic rat dorsal root ganglia neurons to *Clostridium botulinum* neurotoxins," *Toxicon* 38:245-258, Pergamon Press (Feb. 2000).

Besson, J.M., "La complexité des aspects physiopharmacologiques de la douleur," *Drugs 53*:1-9, ADIS Press (1997).

Sharon, N., and Lis, H., "Legume lectins-a large family of homologous proteins," *The FASEB J. 4*:3198-3208, The Federation of American Socieities for Experimental Biology (1990).

Zambenedetti, P., et al., "Identification of lectin binding sites in the rat brain," *Glycoconjugate J. 13*:341-346, Chapman & Hall (1996).

Lis, H., and Sharon, N., "Lectins as Molecules and as Tools,", *Ann. Rev. Biochem,* 55:35-67, Annual Reviews, Inc. (1986).

Kam, C.-M., Office Communication for the U.S. Appl. No. 09/529,130, 8 pages, United States Patent and Trademark Office (mailed on Mar. 1, 2001).

Esmond, R.W., filing for U.S. Appl. No. 09/529,130, 3 pages, "Reply to Restriction Requirement" (filed Apr. 3, 2001).

Kam, C.-M., Office Communication for U.S. Appl. No. 09/529,130, 15 pages, United States Patent and Trademark Office (mailed Aug. 14, 2001).

Esmond, R.W., filing for the U.S. Appl. No. 09/529,130, 51 pages, "Preliminary Amendment and Reply Under 37 C.F.R. §1.111" (filed Dec. 14, 2001).

Kam, C.-M., Office Communication for U.S. Appl. No. 09/529,130, 20 pages, United States Patent and Trademark Office (mailed Mar. 19, 2002).

Chalker, B.E., filing for U.S. Appl. No. 09/529,130, 43 pages, "Amendment and Reply Under 37 C.F.R. § 1.111" (filed Sep. 10, 2002).

Kam, C.-M., Office Communication for U.S. Appl. No. 09/529,130, 11 pages, United States Patent and Trademark Office (mailed Nov. 26, 2002).

Chalker, B.E., filing for U.S. Appl. No. 09/529,130, 14 pages, "Amendment And Reply Under 37 C.F.R. § 1.111" (filed Apr. 25, 2003).

Kam, C.-M., Office Communication for U.S. Appl. No. 09/529,130, 8 pages, United States Patent and Trademark Office (mailed Jul. 7, 2003).

Schwartz, A.L., filing for U.S. Appl. No. 09/529,130, 19 pages, "Amendment and Reply Under 37 C.F.R. § 1.116" (filed Sep. 25, 2003).

Kam, C.-M., Office Communication for U.S. Appl. No. 09/529,130, 3 pages, United States Patent and Trademark Office (mailed Oct. 23, 2003).

Schwartz, A.L., filing for U.S. Appl. No. 09/529,130, 7 pages, "Preliminary Amendment and Reply" (filed Nov. 7, 2003).

Kam, C.-M., Office Communication for U.S. Appl. No. 09/529,130, 13 pages, United States Patent and Trademark Office (mailed Jan. 28, 2004).

Esmond, R.W., filing for U.S. Appl. No. 09/529,130, 7 pages, "Amendment and Reply Under 37 C.F.R. § 1.111" (filed Apr. 28, 2004).

Kam, C.-M., Office Communication for U.S. Appl. No. 09/529,130, 15 pages, United States Patent and Trademark Office (mailed Jul. 9, 2004).

Schwartz, A. L., filing for U.S. Appl. No. 09/529,130, 10 pages, "Amendment and Reply Under 37 C.F.R. § 1.111" (filed Dec. 9, 2004).

Chaddock, J., Declaration Under 37 C.F.R. § 1.132 for U.S. Appl. No. 09/529,130 (filed Dec. 9, 2004).

Foster, K., Declaration Under 37 C.F.R. § 1.132 for U.S. Appl. No. 09/529,130, (filed Dec. 9, 2004).

\* cited by examiner

Lectins and Lectin Conjugates are Analgesic in a Mouse Hot-plate Model

Fig. 13

| Rat | Pretreatment (-4h) | Paw | μl Plasma /100mg tissue |
|---|---|---|---|
| 1. | *Erythrina cristagalli* lectin | Stimulated | 18.4 |
|  | None | Nonstimulated | 4.7 |
| 2. | *Erythrina cristagalli* lectin | Stimulated | 17.5 |
| 3. | Vehicle (Tyrode) | Stimulated | 32.2 |
|  | None | Nonstimulated | 4.3 |

Effect of *Erythrina cristagalli* lectin on neurogenic inflammation induced by stimulation of the rat saphenous nerve.

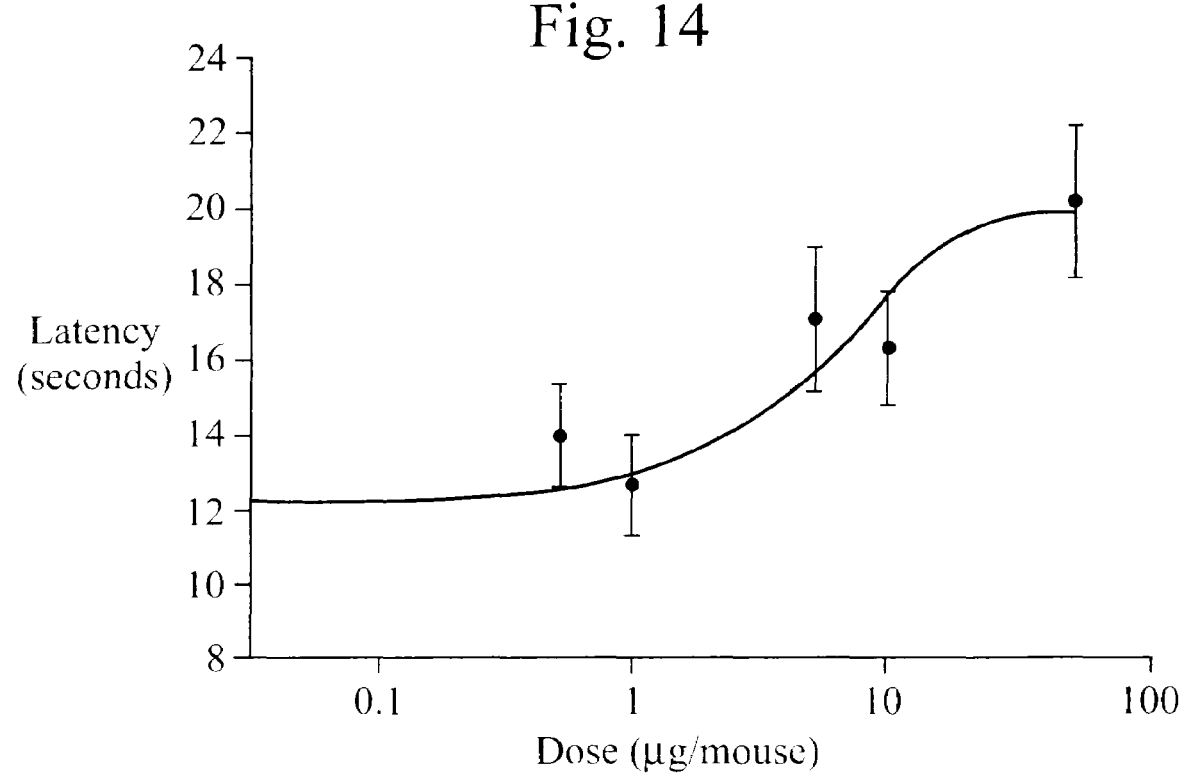

USE OF A LECTIN OR CONJUGATES FOR MODULATION OF C-FIBRE ACTIVITY

The present application is a 371 of PCT/GB00/01247 filed on Mar. 31, 2000, and published in English on Oct. 5, 2000, the disclosure of which is incorporated herein by reference in its entirety.

The present invention relates to the treatment of pain and to compounds that modulate C-fibre activity, in particular the use of these compounds for the treatment of diseases of which C-fibre activity is a component, such as pain, inflammation, psoriasis and other C-fibre related conditions, to methods and compositions therefor and manufacture of those compositions.

A number of disease conditions are known to be related to or associated with activity in C-fibre neurones, in particular pain, inflammation and psoriasis.

C-fibres are small diameter, unmyelinated neurones, which have their sensory termini and cell bodies in the peripheral nervous system (PNS), but which synapse in the dorsal horn of the spinal cord within the central nervous system (CNS). The accepted role of these afferent fibres is to signal strong, injury-threatening (noxious) stimuli or the presence of chemical irritants, including many inflammatory mediators to the CNS. The neurones are thus termed nociceptors. However, the importance of C-fibre neurons in a variety of other clinical conditions is only now emerging.

Uniquely amongst afferent neurones, many C-fibre nociceptors also have efferent, antidromic actions within the peripheral tissue that they innervate. When stimulated, the C-fibres release vasoactive mediators, which have potent actions on local blood vessels and on cells of the immune system. This invariably results in the phenomenon termed neurogenic inflammation. C-fibre efferent neurones store and co-release upon stimulation the neuropeptides substance P(SP) and calcitonin gene related peptide (CGRP). Both of these peptides are potently vasoactive and the blood vessel dilation by CGRP combined with an increase in SP induced vascular permeability results in plasma extravasation and peripheral oedema. This in turn recruits infiltration by eosinophils and other inflammatory cells and subsequently the full panoply of an inflammatory cascade.

Most citations report neurogenic inflammation in the skin. However, C-fibres are distributed widely throughout the body. In bronchial airway tissues, substances released from nociceptive terminals may cause smooth muscle contraction and also trigger the secretion of mucus. Detailed information is also available for C-fibre mediated effects in the bladder and the gastrointestinal tract. Neurogenic inflammation has now been clearly associated with a variety of disorders including asthma, ulcer formation and headache. It may also be a component of generalised inflammatory responses such as arthritis.

Psoriasis is a hyperproliferative epidermal disease whose aetiopathogenesis remains largely undefined. However, one of the most favoured hypothesises is that the condition correlates with an altered release of SP and CGRP neuropeptides by sensory efferent neurones.

Studies of neurogenic inflammation in psoriatic skin have demonstrated that morphological contact between mast cells and sensory C-fibres increases in developing (1–3 weeks) psoriatic lesions when compared to non-lesional controls. This increase reaches statistical significance in mature lesions. It is considered that the associated increase in neurogenic stimulation promotes mast cell degranulation and the release of inflammatory mediators. This in turn allows entry into the lesional dermis of various mediators that interact with keratinocytes to promote the hyperproliferation characteristic of psoriatic plaques.

A variety of psoriasis treatments are available ranging from moisturising creams, phototherapy and topical vitamin applications to corticosteroids and immune suppressants. However, none of these are universally effective nor do they appear to treat the underlying causes of the disease. Furthermore, the most effective treatments, especially for conditions requiring intensive therapy, have unpleasant and often toxic side effects.

Pain can be classified in a number of ways depending upon the cause, the mechanism of action and the duration of suffering. Pain can also be categorised by the level of discomfort, e.g. mild, moderate or severe. Most pain is caused by direct mechanical, thermal or chemical damage to specific sensory receptors (nociceptors) which are located in the skin, muscle, some viscera and a number of other tissues. The perception of "feeling pain" follows the transduction and transmission of a noxious stimulus from the site of this insult or damage to the higher centres of the Central Nervous System (CNS).

Transduction of the majority of pain signals arises from the activation of small diameter, thinly myelinated or non-myelinated neurones known as $A_\delta$- and C-fibres respectively. These fibres have their cell bodies in the dorsal root ganglia, juxtaposed along the length of the spinal column. They synapse primarily in dorsal horn laminae I and II of the spinal cord. The most common nociceptors are innervated by C-fibres.

The transmission of a pain stimulus (nociception) is a complex process. There are many chemical transmitters involved at the site of insult and throughout the Peripheral Nervous System (PNS) and CNS. For each of these chemical transmitters there is also an associated receptor, or group of receptors, which transduce and transmit the pain impulse.

Receptors can be designated as either excitatory or inhibitory. Activation of excitatory receptors causes neuronal firing, resulting in either an increase in neurotransmitter release or an increase in the excitability of neurones. In contrast, activation of inhibitory receptors causes a decrease in neuronal firing, a reduction in transmitter release and may cause a reduction in neurone excitability.

The interaction of pain neurotransmitters with their receptors provides a large number of potential intervention points for novel therapies for the treatment of pain. Each element, receptor, chemical mediator, neurotransmitter, ion channel and synapse, in this complex pathway is a potential target for blockade.

WO96/33273 describes toxin conjugates comprising a clostridial neurotoxin component and a Targeting Moiety selected to target peripheral sensory afferents. The clostridial neurotoxin component of the conjugate possess a protease activity specific for components of the neurosecretory machinery (see Claim 1). Amongst a large number of potential Targeting Moieties (see pages 24 and 25), lectins are listed (see line 12 on page 13).

EP-A-602686 describes the use of lectin concentrates obtained from mistletoe in raising the natural immune resistance in humans and mammals, and/or for tumour therapy. In more detail, the lectin concentrates contain a high proportion of immunologically active galactose-specific lectin designated ML1.

The current analgesic standards are the opiates, for example morphine. While these compounds are effective in a range of pain conditions, they do not provide a panacea. Their effects are short lived, thus requiring frequent application. Furthermore, there are associated unpleasant side effects of respiratory depression, nausea, dependency, addiction and induction of tolerance.

Activity of C-fibres is also implicated in the modulation of mucus release in disease conditions such as those involving mucus hypersecretion.

It is an object of the present invention to provide new methods and compositions for treatment of pain and for treatment of C-fibre related disease conditions such as inflammation, psoriasis, mucus hypersecretion and pain.

Accordingly, a first aspect of the invention provides the use of a lectin in manufacture of a medicament for modulation of C-fibre neurone activity. The first aspect of the invention also provides a method of modulating C-fibre activity by administering an effective amount of lectin.

In use of an embodiment of the invention, a lectin administered in a pharmaceutical composition binds to a C-fibre neurone and inhibits transmission of nerve cell impulses via that neurone, treating and thereby reducing a disease condition caused by or involving excessive activity of that C-fibre neurone.

Oligosaccharide carbohydrate receptors regulate key stages in many physiological processes of pharmaceutical importance such as inflammation, oncology, immunology, neural, infectious and other types of diseases (Edmonds, B, J. and Koenig, E. [1990] *Cell Motil. Cytoskeleton,* 17, 106–17; Edmonds, B, J. and Koenig, E. [1991] *J. Neurocytol.* 20, 232–47; Gupta, D., Arango, R. and others [1994] *Biochemistry,* 33, 2503–08). Lectins are a class of proteins, often glycoproteins, that bind to carbohydrate structures and are known to agglutinate cells and/or precipitate complex carbohydrates. Two publications describing how lectins bind to neuronal cells are Silverman, J. D. and Kruger, L. (1990), selective neuronal glycoconjugate expression in sensory and autonomic ganglia: relation of lectin reactivity to peptide and enzyme markers, *J. Neurophysiol.* 19, 789–801; and Streit, W. J., Schulte, B. A., Balentine, D. and Spicer, S. S. (1985), histochemical localization of galactose-containing glycoconjugates in sensory neurons and their processes in the Central and Peripheral Nervous System of the rat, *J. Histochem. Cytochem.* 33, 1042–52. Lectins can be isolated from a wide range of natural sources including seeds, plant roots and bark, fungi, bacteria, seaweed and across the whole range of life forms from viruses to mammals. Some antibodies may mimic the in vivo activity of lectins. The most commonly exploited sources of lectins are the seeds of plants. The precise physiological role of lectins in nature is still unknown, but they have proved to be very valuable in a wide variety of applications in vitro including blood grouping and histochemical staining for cell surface markers. It is known in the literature that lectins have demonstrable selectivity for cells of different origin.

Due to the ubiquitous nature of oligosaccharide structures, lectins bind to a large number of cells. However, because of the known complexity and specificity of the transduction and transmission pathways of C-fibre neurones, it is particularly surprising and unexpected that lectins can bind to neurones so as to modulate C-fibre and/or $A_\delta$-fibre activity. For the purposes of this invention a "lectin" or a "lectin domain" is the whole of or that part of a peptide, protein or glycoprotein, or mimic thereof, that has the ability to bind specifically to mono- or oligosaccharide structures. The invention is of application without limit to particular sub-groups of lectins, though preferred lectins are those that bind galactosyl residues, for example terminal β-D-galactosyl or terminal α-D-galactosyl residues or N-acetylgalactosamine residues, or glucosyl residues.

In use of an embodiment of the invention, a lectin binds to a surface structure or structures (the Binding Site [BS]) which is characteristic of, and has a degree of specificity for relevant sensory effector cells and/or neurones in the peripheral or central nervous system responsible for the afferent or projection transmission of pain or the regulation of said transmission. Next, it modulates the function of such cells so that either the transduction or transmission of the pain signal is reduced or abolished. Such modulation may be due to suppression of the activity of afferent and or projection neurones or due to promotion of the activity of inhibitory neurones.

One aspect of the invention thus advantageously provides a further class of analgesic compositions and uses of these compositions for treatment of pain. The invention provides use of a lectin in manufacture of a medicament for treatment of pain and a method of treatment of pain comprising administration of an effective amount of a lectin. In specific embodiments of the invention, lectins have been tested using the mouse hot plate model—an industry standard model acknowledged as predictive of human response—and found to be analgesic. The mouse hot-plate model is acknowledged as a model for human pain in Heilman, R. D. et al. (1976): An evaluation of the hot plate technique to study narcotic analgesics. *Res. Comm. Chem. Pathol. Pharmacol.* 13 (4), 635–647.

The lectin applications of the present invention have demonstrated equivalent latency, prolonged duration and equivalent potency when compared with the analgesic effects of morphine.

In a specific embodiment of the invention a galactoseries-specific lectin is extracted from the coral tree *Erythrina cristagalli* and administered intrathecally, exhibiting strong analgesic activity. In a further specific embodiment of the invention a galactoseries-specific lectin is extracted from the coral tree *Erythrina corallodendron* and administered intrathecally, also exhibiting strong pain-reducing activity. These illustrative lectins are heterodimeric and homodimeric glycoproteins respectively of approximate molecular weight of 60 kDa (Arango, R. and others [1992] *Eur. J. Biochem.* 205, 575–81). In a still further specific embodiment of the invention, a glucosyl-specific lectin is analgesic in the mouse hot plate model.

A list of commercially available lectins appears in the 1998 Sigma catalogue. A further example of a lectin, specifically a bacterial lectin is PA-I from *Pseudomonas aeruginosa*. This is a D-galactose binding lectin with a molecular weight of 13 kDa (Garber, N., Guempel, U. and others (1992). *Biochim. Biophys. Acta.* 1116, 331–3).

In use of a further embodiment of the invention, a lectin binds to a C-fibre neurone that innervates a psoriatic lesion and inhibits release of inflammatory modulators, including substance P. A further aspect of the innovation thus advantageously provides a class of compositions for treatment of psoriasis.

In use of a still further embodiment of the invention, a lectin binds to a C-fibre neurone which modulates mucus release or control of mucus release. A still further aspect of the invention thus advantageously provides a class of composition and uses thereof for treatment of mucus hypersecretion.

Site and mode of delivery of lectin is typically a factor in obtaining the desired therapeutic effect. Thus, a topically and/or specifically delivered composition containing a lectin can comprise a lectin that binds to C-fibres but is not specific for C-fibres. By way of example, an embodiment of the invention provides for treatment of a localised disease condition such as psoriasis, using a lectin formulated in a cream which can be topically applied or a lectin formulated for sub-dermal injection. In this way, delivery of a lectin according to the invention is targeted and not systemic. In the case particularly of formulations for injection, it is optional to include a further pharmaceutically active substance to assist retention at or reduce removal of the lectin from the site of administration, and one example is the use of a vasoconstrictor such as adrenaline. Such a formulation confers the advantage of increasing the residence time of lectin following administration and thus increasing and/or enhancing its effect.

Similar targeting delivery is appropriate for diseases involving C-fibre activity and for which the active lectin can be delivered via aerosol or other spray. An aerosol formulation of a lectin enables delivery to the lungs and/or other nasal and/or bronchial or airway passages, facilitating use of lectin for treatment of diseases such as mucus hypersecretion and rhinitis (hay fever).

Generally, the invention is of application to treatment of diseases caused by or exacerbated by antidromic activity in C-fibres, by inhibition of the antidromic activity, which is typically at least partially self-perpetuating or of an origin that is not clearly defined or presently understood. More specifically, the compounds and formulations of the invention can be used for treatment of inflammation including neurogenic inflammation, erythema, irritable bowel syndrome, headache, asthma, arthritis and as already mentioned pain including migraine.

Lectins and lectin domains may be arranged, covalently or non-covalently, so as to form oligomers and/or polymers, their functional units optionally separated using linkages which may include one or more spacer arms. The chemical conjugation and genetic fusion of such domains can be achieved by conventional methods. Lectins and lectin domains may be coupled to a distinct, additional, lectin or non-lectin companion protein forming a multi-component agent such that the efficacy of the agent is enhanced when compared to the native lectin component alone. Such an agent is optionally the expression product of a recombinant gene which provides for a minimal functional peptide domain such that the agent may be monomeric in form and may optionally be glycosylated. The agent may be the expression product of a recombinant gene delivered independently to the preferred site of action of the agent. Gene delivery technologies are widely reported in the literature (reviewed in "*Advanced Drug Delivery Reviews*" Vol. 27, [1997, Elsevier Science Ireland Ltd].

Methods for extracting and purifying lectins are known in the literature, for example, Iglesias, J. L., Lis, H. and Sharon, N. (1982) *Eur. J. Biochem.* 123, 247–252.

Gene expression technologies for the provision of functional, recombinant lectins, both glycosylated and non-glycosylated, are known in the literature (Arango, R. and others [1992] *Eur. J. Biochem.* 205, 575–81). By way of example, a cDNA encoding a lectin can be cloned into any of the pET series of plasmid vectors. Expression of the gene is thus under control of the T7 promoter and can be well regulated in the *E. coli* host. The expression product is recovered and purified from inclusion bodies using established techniques. These methods have been shown to produce non-glycosylated lectin proteins that otherwise retain all of the known functions of the native lectins.

Recombinant lectin protein fusions may be made by a variety of approaches. For example, the fusion of a gene coding for a lectin to a gene coding for a second lectin or non-lectin protein. These gene fusions may be separated by a further nucleic acid sequence coding for a flexible linker region (e.g. a polyglycine tract) which facilitates interaction of the fused proteins either with themselves (oligomerisation) or with other target molecules (receptors, other lectins etc.).

The lectin may further be expressed in single copy or multicopy arrangements on the surface of bacteriophage such that the monomers may associate to form a functional oligomeric molecule. In some instances, functionality may request the association of two or more separate bacteriophage displaying or require expressing lectin monomers. This approach may also be used for the expression of lectin fusion proteins.

The present invention further provides a composition comprising a lectin as described coupled to another peptide or protein. The peptide or protein may be a carrier or may impart a second function to the composition in addition to the C-fibre modulatory properties of the lectin. The peptide or protein may itself have a C-fibre and/or $A_\delta$-fibre modulatory property. The modulatory property of the peptide or protein may be independent from that of the lectin. Alternatively, the peptide or protein may modify the C-fibre and/or $A_\delta$-fibre modulatory property of the lectin.

The peptide or protein may be any molecule which is substantially free from Clostridial neurotoxin enzyme activity. Consistent with this definition, the peptide or protein may be, for example, a non-Clostridial toxin of plant or microbial origin, including but not limited to bacterial toxins. Further Examples of suitable peptides or proteins include inactive $LH_N/A$ (ie. inactive Clostridial neurotoxin), a second lectin (which may be the same as the first lectin or different), or multiple lectin conjugates (eg. dimers or trimers, etc).

Thus, the lectin molecule of the present invention may be employed as a targeting moiety to direct the peptide or protein to relevant sensory effector cells and/or neurones in the PNS or CNS responsible for the afferent or projection transmission or pain or the regulation of said transmission. The peptide or protein may then exert a C-fibre and/or $A_\delta$-fibre modulation property at the target site.

The lectin of the present invention helps the in vivo stabilization of the peptide or protein.

In one embodiment, the present invention provides a composition comprising a first lectin conjugated to a second lectin, the lectins being Optionally different or the same. All conjugate embodiments of the present invention may be coupled directly or via an intermediate linker. The lectins of the invention may also be modified to make derivatives, for example modified to remove a carbohydrate group whilst maintaining its ability to bind target cells.

In another embodiment, the peptide or protein is an endopeptidase, suitably of Clostridial origin. Specifically, the lectin of the invention can be coupled to an endopeptidase from a clostridial species, optionally from botulinum neurotoxin type A, or B. Such compositions are conveniently made by coupling a galactose-binding lectin to an enzymatically active fragment of a Clostridial neurotoxin, for example an $LH_N$ fragment of a botulinum neurotoxin, and in an illustrative example set out below a galactose-binding lectin from *Erythrina cristagalli* is coupled to an $LH_N$ fragment of botulinum neurotoxin type A. The present invention thus still further provides a method of preparing a composition of the invention by covalently attaching a lectin to another peptide or protein.

The lectin of the invention either in isolated form or incorporated into compounds or compositions may exert its activity by preventing the release of a neurotransmitter or neuromodulator from a primary sensory afferent, by inhibiting the release of a neurotransmitter or neuromodulator from a primary nociceptive afferent, by inhibiting the release of a neurotransmitter or neuromodulator from a projection neurone, by promoting the activity of an inhibitory neurone or by a combination thereof.

The lectin of the invention may be optionally modified such that it possesses minimal or substantial no C-fibre and/or Aδ-fibre modulation property. However, in this embodiment, the lectin either retains or possesses a targeting specificity to relevant sensory effector cells and/or neurones in the PNS or CNS which is preferably at least comparable with that of unmodified lectin. Thus, in this embodiment, the lectin simply targets the peptide or protein. Such modification may be achieved, for example, by random mutagenesis or site-directed mutagenesis of lectin- or conjugate-encoding nucleic acid or by direct chemical modification of the lectin or lectin conjugate.

In another aspect of the present invention, the peptide or protein is not coupled to the lectin. According to this embodiment, it is however preferred that the peptide or protein is associated with the lectin by, for example, a non-covalent linkage, an electrostatic interaction and/or Van der Waal's forces.

To this end, the lectin and/or the peptide or protein may be modified by introducing complementary surface charges which facilitate association of the two components in vitro and in vivo. Such modification may include introducing positively or negatively charged groups (eg. chemical groups or amino acid groups) into exposed surfaces on either or both of the two components.

Another aspect of the invention lies in a method of modulating C-fibre activity comprising administering an effective amount of a lectin to a patient. The lectin can be used to inhibit C-fibre activity, or to stimulate C-fibre activity.

Further aspects of the invention lie in a composition for modulation of C-fibre activity comprising a nucleic acid encoding a lectin, a method of modulating C-fibre activity comprising administering an effective amount of such a composition, and use of such a composition in manufacture of a medicament for modulation of C-fibre activity.

In a yet further aspect, the invention provides a pharmaceutical composition for modulation of C-fibre neurone activity, comprising
  a lectin or a composition according to any of the above aspects of the invention; and
  at least one of a pharmaceutically acceptable carrier, excipient, adjuvant, propellant and or salt.

The compound may thus be formulated for oral, parenteral, continuous infusion, inhalation or topical application and encompasses delivery of the lectin or conjugate its nucleic acid coding sequence or its agonists. Intraspinal injection is another route of administration, though the present invention encompasses also any administration that delivers the compound to an appropriate or optimal site of intervention. Administration might take advantage of a variety of delivery technologies including microparticle encapsulation, viral delivery systems or high pressure aerosol impingement, including delivering a lectin-coding nucleic acid to a cell population in which it would be expressed and the gene product would be capable of effecting analgesia. Additionally, the target cells for lectin activity need not be the cells in which the gene is expressed.

Agents of the invention for treatment of pain may be administered to a patient by intrathecal or epidural injection in the spinal column at the level of the spinal segment involved in the innervation of an affected organ. This is, for example, applicable in the treatment of deep tissue pain, such as chronic malignant pain. The dosage ranges for administration of the compounds of the present invention are those to produce the desired therapeutic effect. It will be appreciated that the dosage range required depends on the precise nature of the lectin or composition, the route of administration, the nature of the formulation, the age of the patient, the nature, extent or severity of the patient's condition, contraindications, if any, and the judgement of the attending physician. Wide variations in the required dosage, however, are to be expected depending on the precise nature of the agent. Variations in these dosage levels can be adjusted using standard empirical routines for optimisation.

Fluid dosage forms are typically prepared utilising the compound and a pyrogen-free sterile vehicle. The compound, depending on the vehicle and concentration used, can be either dissolved or suspended in the vehicle. In preparing solutions the compound can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving. Advantageously additives such as buffering, solubilising, stabilising, preservative or bactericidal, suspending or emulsifying agents and or local anaesthetic agents may be dissolved in the vehicle.

Dry powders, which are dissolved or suspended in a suitable vehicle prior to use, may be prepared by filling pre-sterilised drug substances and other ingredients into a sterile container using aseptic technique in a sterile area. Alternatively the drug and other ingredients may be dissolved into suitable containers using aseptic technique in a sterile area. The product is then freeze dried and the containers are sealed aseptically.

Compositions suitable for administration via spinal injection may be made up in a conventional manner and employed in conjunction with conventional administration devices.

Compositions of the previously filed International patent application PCT/GB98/03001 that contain lectins may be used in the present invention but are excluded from the scope of compositions claimed herein.

There now follows description of specific embodiments of the invention, illustrated by drawings in which:

FIG. 13 illustrates antidromic effects of the *Erythrina cristagalli* lectin.

FIG. 14 Inhibition of response to painful thermal stimuli following application of *Erythrina cristagalli* to the mouse spinal cord in vivo.

Figure 2:
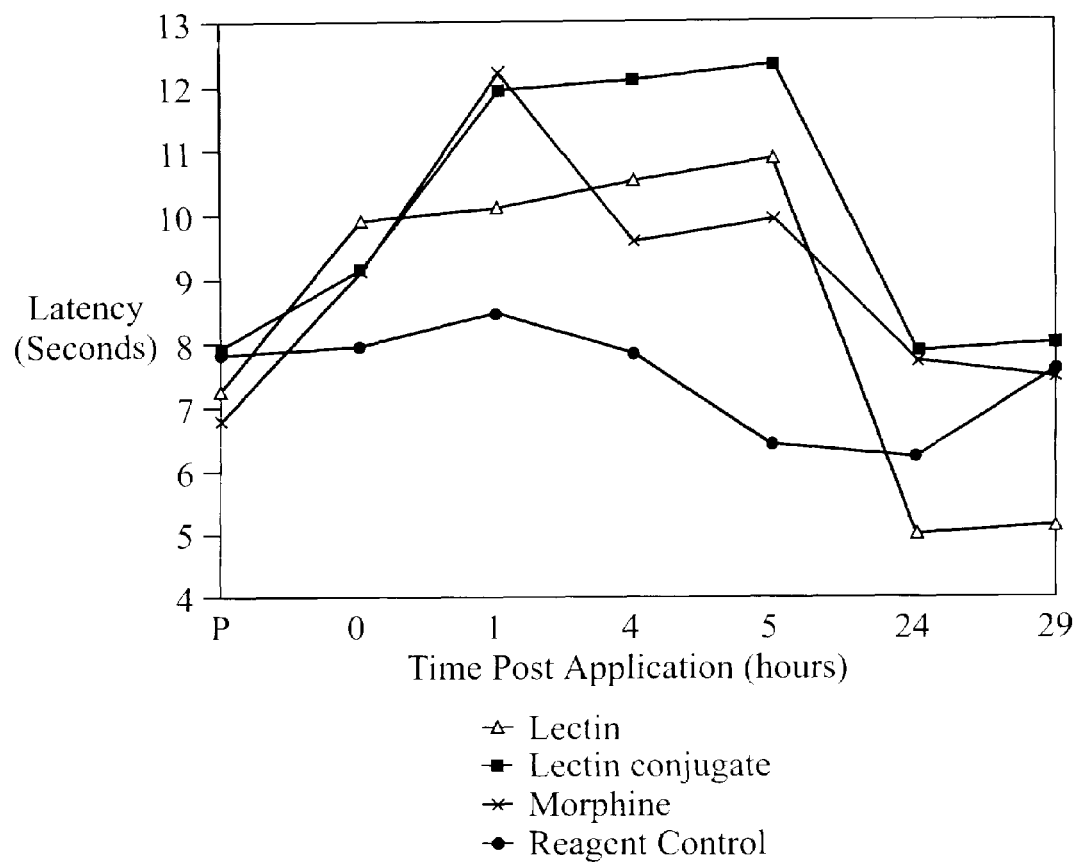
FIG. 2 shows the analgesic effect of *Erythrina cristagalli* lectin in mice in a hot-plate model.

Some of the above Figures are now described in more detail below:

In FIG. 2, lectin was applied intrathecally (30 μg in a 5 μl vehicle volume). Onset of lectin-induced analgesia reaches a plateau at 1 hour post application and remains constant for at least 5 hours. Morphine achieves a maximal effect at 1 hour and then returns to control levels over a period of 5 hours. (Data is the mean of replicate readings from groups of 10 mice±SE).

Figure 3:
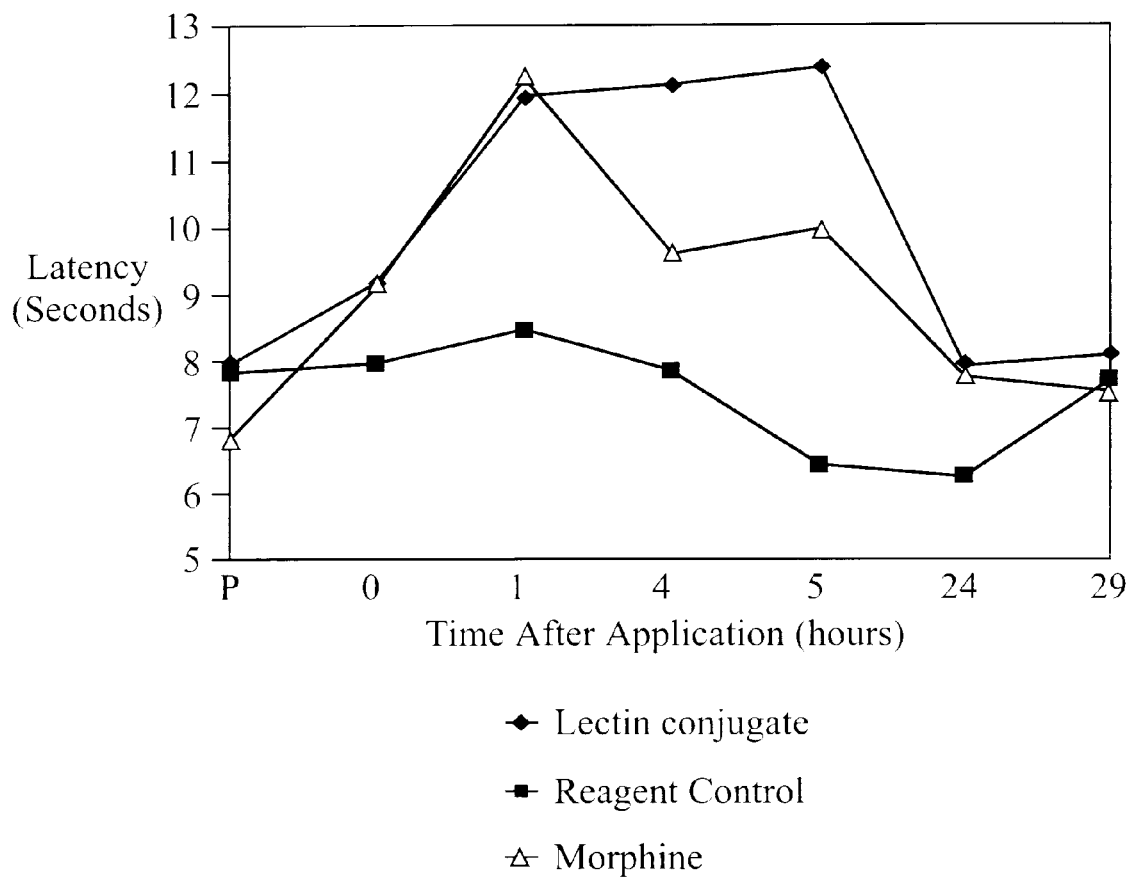
FIG. 3 shows the analgesic effect of lectin-conjugates is comparable to a supramaximal dose of morphinein mice in a hot-plate model.

In FIG. 3, lectin-conjugate was applied intrathecally (30 μg in a 5 μl vehicle volume). Onset of lectin-conjugate induced analgesia reaches a plateau at 1 hour post application and remains constant for at least 5 hours. Lectin-conjugate analgesia is similar to a supramaximal dose (20× EC50) of morphine in this test, but is of much longer duration; morphine achieves a maximal effect at 1 hour and then returns to control levels over a period of 5 hours. (Data is the mean of replicate readings from groups of 10 mice±SE).

Figure 6:
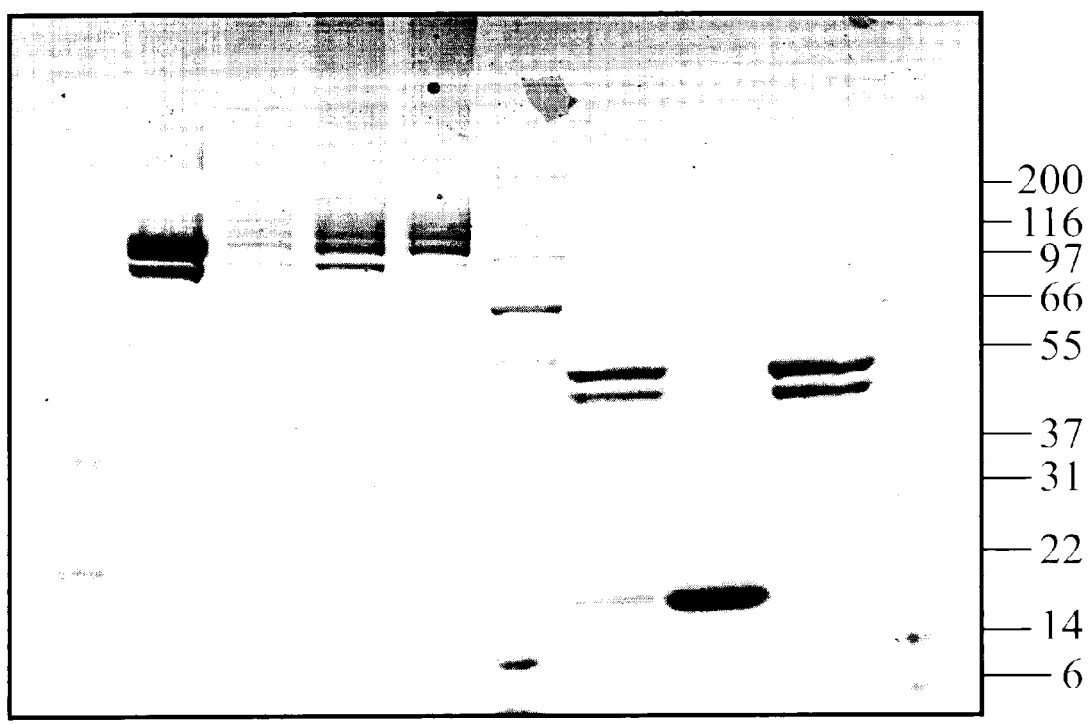
FIG. 6 illustrates SDS-PAGE analysis of a conjugate of wheat-germ agglutinin lectin and a companion protein ($WGA-LH_N/A$)

In FIG. 6, protein fractions were subjected to 4–20% polyacrylamide SDS-PAGE prior to staining with Coomassie blue. Lanes 6–8 were run in the presence of 0.1M DTT. Lanes 1 (&7) and 2 (& 8) represent derivatised WGA and derivatised $LH_N/A$ respectively. Lanes 3–5 represent conjugation mixture, post-Superose-12 chromatography and post GlcNAc-affinity chromatography respectively. Lanes 6 represents a sample of reduced final material. Approximate molecular masses (kDa) are indicated on the Figure.

Figure 7:
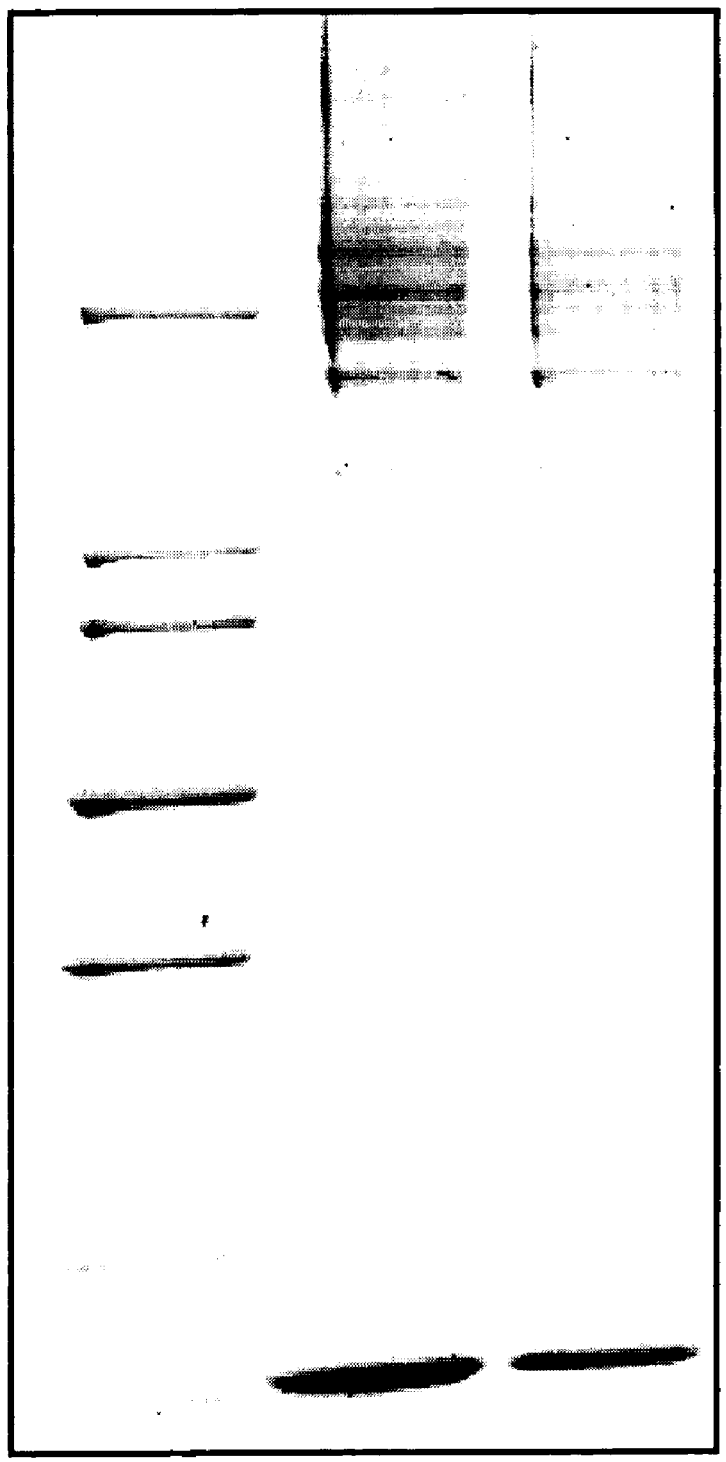
FIG. 7 illustrates non-reducing SDS-PAGE analysis of a purified conjugate of *Erythrina corallodendron* lectin and a companion protein ($ECorL-LH_N/A$)

In FIG. 7: Lane 1=molecular weight markers; Lane 2=post-affinity purified sample; and Lane 3=pre-affinity purified sample.

Figure 8:
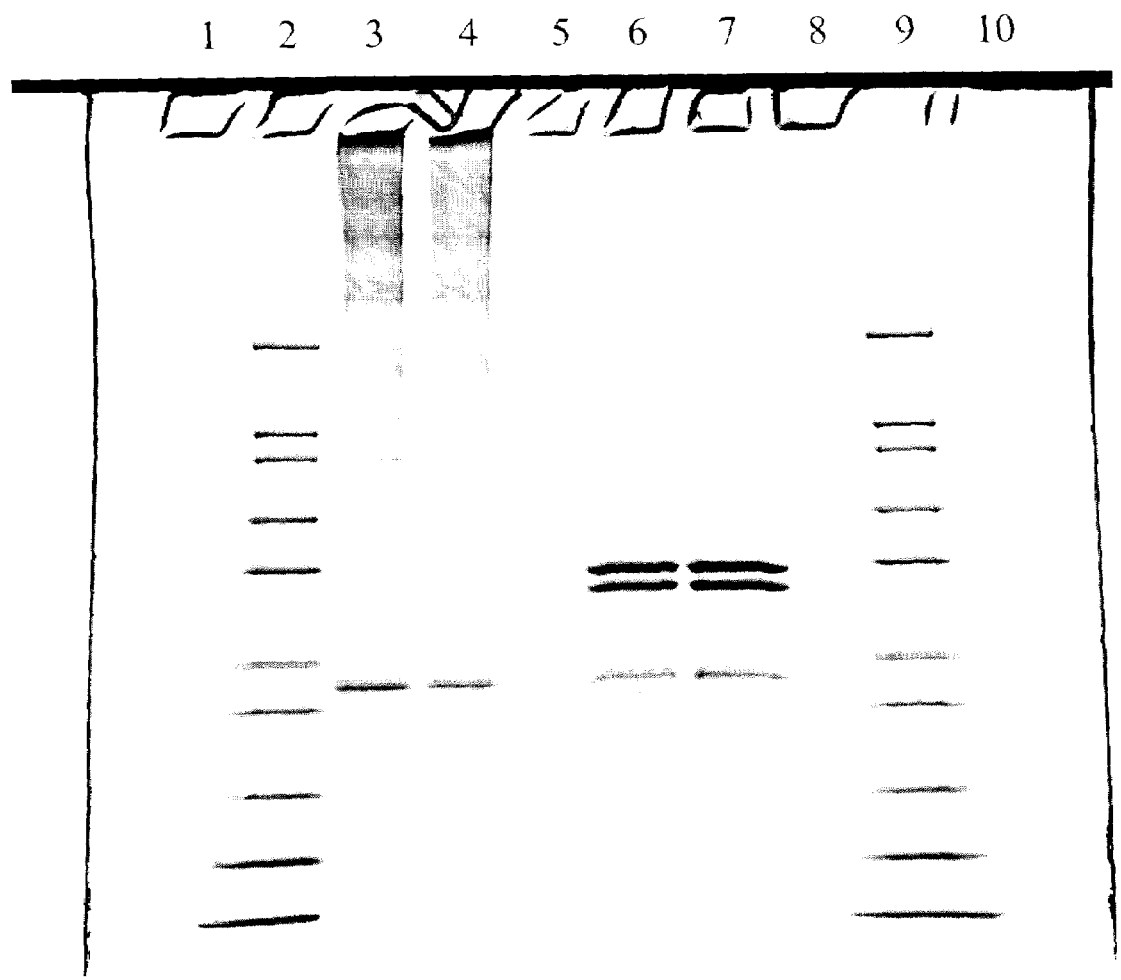
FIG. 8 illustrates SDS-PAGE analysis of a purified conjugate of *Bandeiraea simplicifolia* and a companion protein ($IB_4-LH_N/A$)

In FIG. 8: Lanes 2 & 9=molecular markers (Novex, Mark 12); Lanes 3 & 4 $IB_4$-$LH_N/A$; and Lanes 6 & 7=$IB_4$-$LH_N/A$ reduced by addition of 0.1M DTT.

Figure 9:
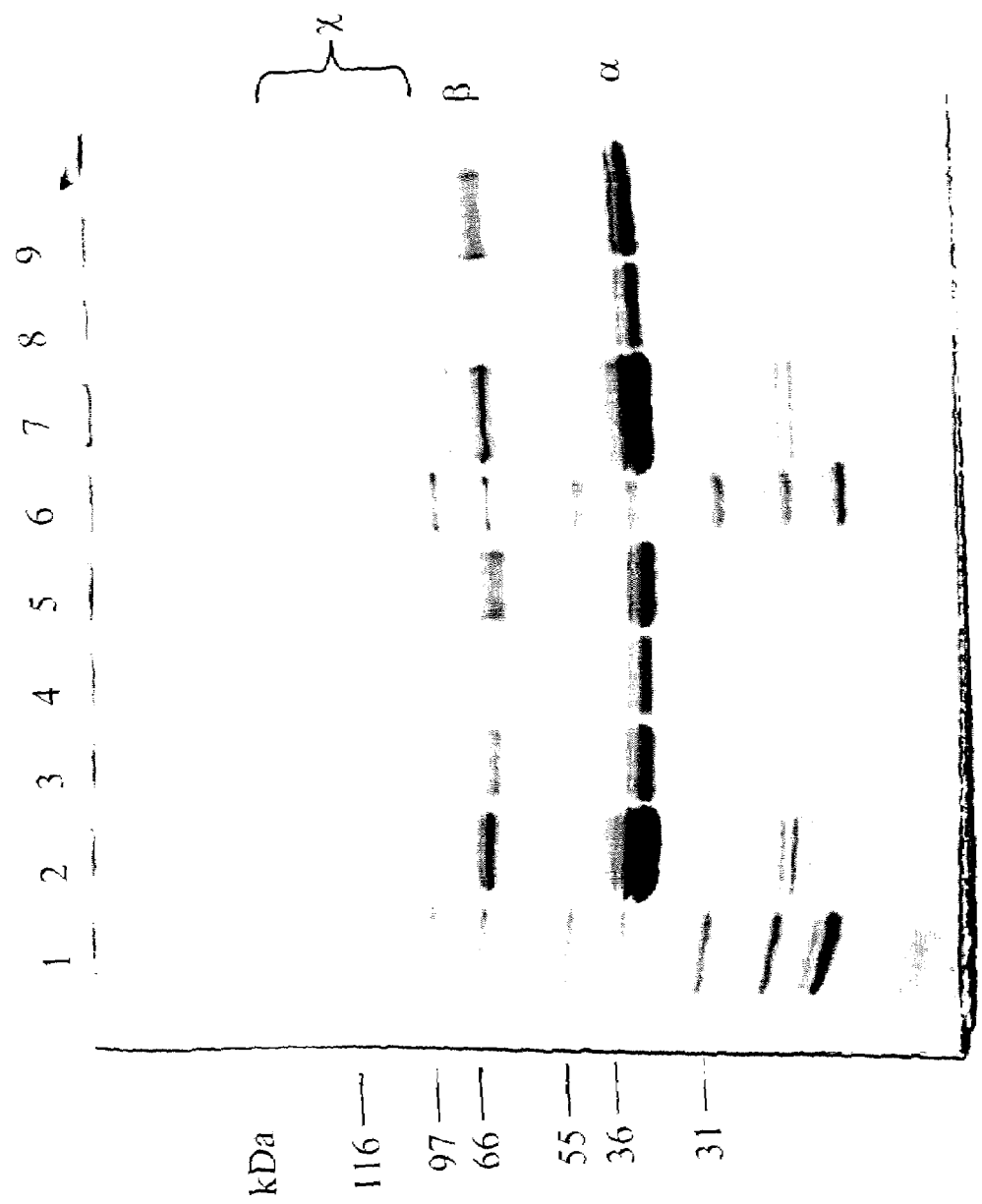
FIG. 9 illustrates SDS-PAGE analysis of conjugated oligomeric *Erythrina cristagalli* lectin (ECL)

In FIG. 9: α represents lectin monomers; β represents lectin dimers; χ represents lectin oligomers; Lane 1=Mark 12 molecular markers; Lane 2=ECL; Lane 3=ECL derivatised with SMPB; Lane 4=ECL derivatised with SPDP; Lane 5=non-reduced oligomeric ECL—ECL mix; Lane 6=Mark 12 molecular markers; Lane 7=Reduced SMPB-derivatised ECL; Lane 8=Reduced SPDP-derivatised ECL; and Lane 9=Reduced ECL—ECL conjugate mix.

Figure 10:
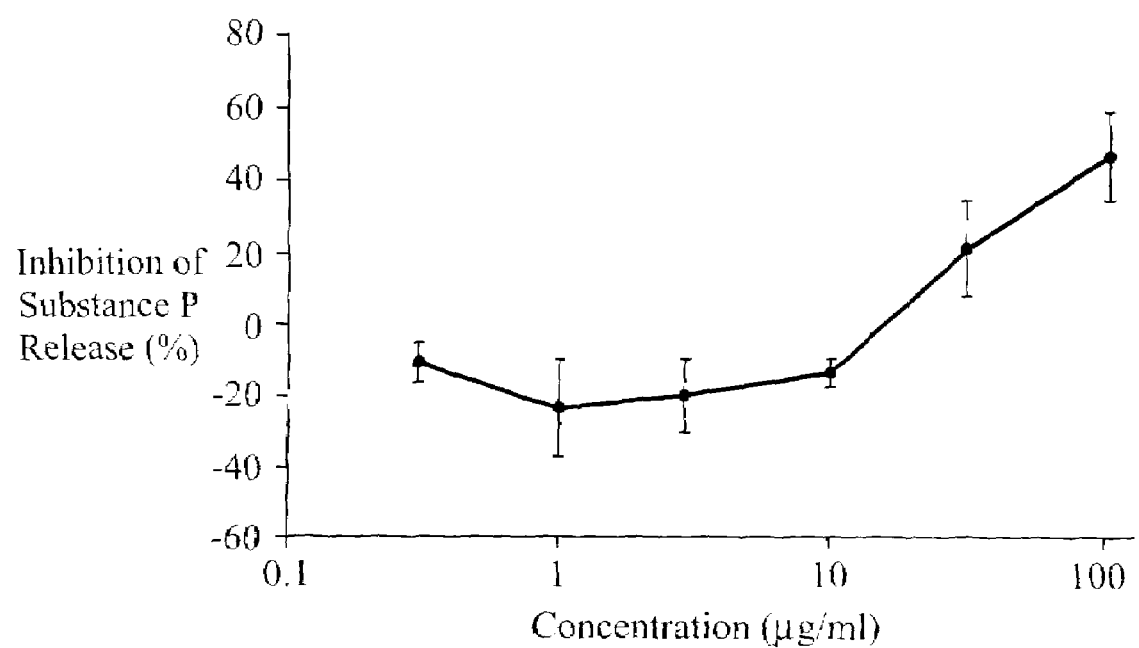
FIG. 10 illustrates modulation of substance P release by *Erythrina cristagalli* lectin.

In FIG. 10, data are presented as the mean of at least three determinations±SEM.

Figure 11:
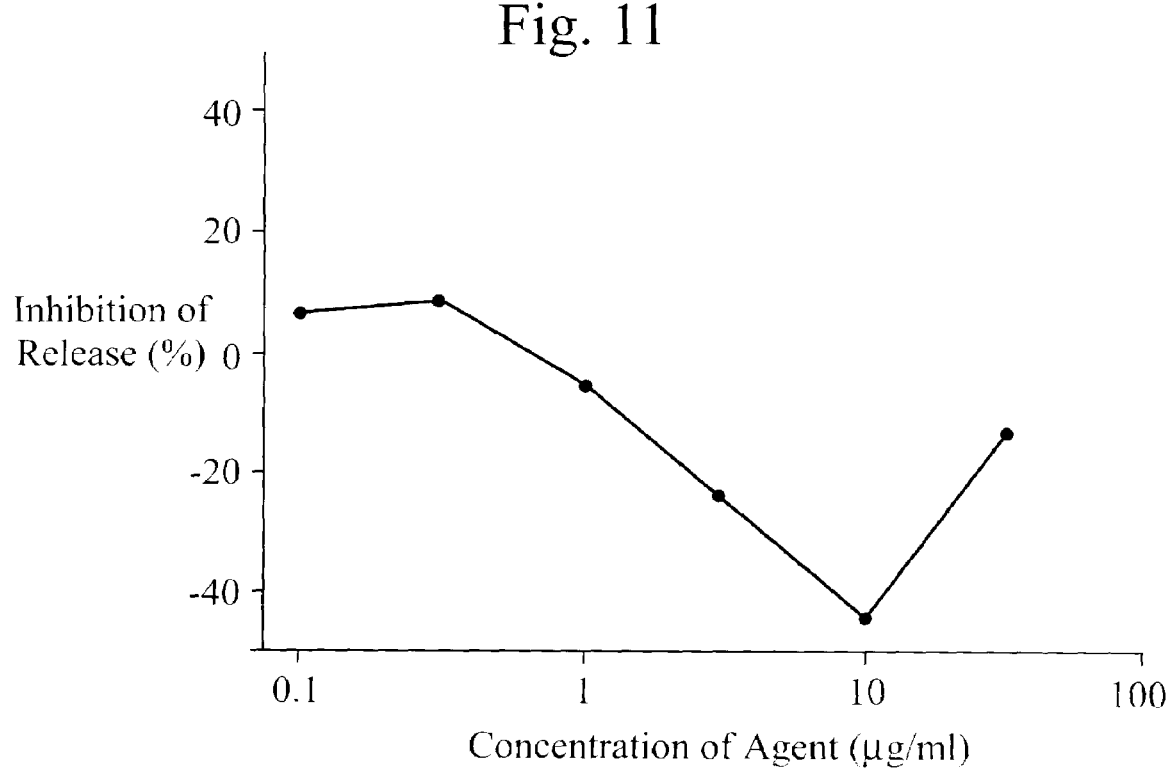
FIG. 11 illustrates modulation of substance P release by *Erythrina cristagalli* lectin conjugated to another protein ($LH_N/A(-)$)

In FIG. 11, conjugate was applied to eDRG neurons for three days prior to determination of the release of substance P. Released substance P was related to controls to determine % release;

The invention thus provides lectins and lectin derivatives useful inter alia for the treatment of pain and components for synthesis of molecules as described in WO94/21300, WO96/33273, and WO99/17806.

EXAMPLE 1

Preparation of *Erythrina Cristagalli* Lectin.

Lectins from *E. cristagalli* may be prepared as described by Iglesias, J. L., Lis, H. and Sharon, N. (1982) *Eur. J. Biochem.* 123, 247–252. Alternatively the purified lectin may be purchased from a range of suppliers such as Sigma.

EXAMPLE 2

Method for the Preparation of Oligomers of *Erythrina Cristagalli* Lectin.

Materials

*E. cristagalli* lectin (ECL) was obtained from Sigma Ltd. SPDP was from Pierce Chemical Co. PD-10 desalting columns were from Pharmacia. Dimethylsulphoxide (DMSO) was kept anhydrous by storage over a molecular sieve. Denaturing sodium dodecylsulphate polyacrylamide gel electrophoresis (SDS-PAGE) was performed using gels and reagents from Novex. Immobilised lactose-agarose was obtained from Sigma Ltd. Additional reagents were obtained from Sigma Ltd.

Method

The lyophilised lectin was rehydrated in phosphate buffered saline (PBS; 10 mM $Na_{2\ HPO4}$, 140 mM NaCl, 2.7 mM KCl, 1.8 mM $KH_2PO_4$, pH7.3) to a final concentration of 10 mg/ml. Aliquots of this solution were stored at −20° C. until used.

For conjugation the lectin was reacted with an equal concentration of SPDP by the addition of a 10 mM stock solution of SPDP in DMSO with mixing. After one hour at room temperature the reaction was terminated by desalting into PBS over a PD-10 column.

From one aliquot of the SPDP derivatised lectin material the thiopyridone leaving group was removed by reduction with dithiothreitol (DTT, 5 mM, 30 min). The product of this reaction was analysed spectrophotometrically at 280 nm and 343 nm to determine the degree of derivatisation achieved. The degree of derivatisation achieved was 0.8±0.06 mol/mol. The thiopyridone and DTT were removed by once again desalting into PBS over a PD-10 column.

A second aliquot of SPDP derivatised lectin material protein was desalted into PBSE (PBS containing 1 mM EDTA).

The bulk of the derivatised ECL lectin and the DTT treated derivatised ECL were mixed in proportions such that the DTT treated derivatised ECL was in greater than three-fold molar excess. The oligomerisation reaction was allowed to proceed for >16 h at 4° C.

The product mixture was centrifuged to clear any precipitate that had developed. The supernatant was concentrated by centrifugation through concentrators (with 10000–50000 molecular weight exclusion limit), dialysed against PBS, and stored at 4° C. until use.

The oligomerisation products were analysed by SDS-PAGE on 4–20% polyacrylamide gradient gels, followed by staining with Coomassie Blue.

EXAMPLE 3

Method for the Preparation of a Conjugate Between *Erythrina Cristagalli* Lectin and a Companion Protein.

Materials

*E. cristagalli* lectin (ECL) was obtained from Sigma Ltd. The companion protein in this example is a clostridial enzyme designated $LH_N/A$ and was prepared essentially by the method of Shone C. C., Hambleton, P., and Melling, J. 1987, *Eur. J. Biochem.* 167, 175–180. SPDP was from Pierce Chemical Co. PD-10 desalting columns were from Pharmacia. Dimethylsulphoxide (DMSO) was kept anhydrous by storage over a molecular sieve. Denaturing sodium dodecylsulphate polyacrylamide gel electrophoresis (SDS-PAGE) was performed using gels and reagents from Novex. Immobilised lactose-agarose was obtained from Sigma Ltd. Additional reagents were obtained from Sigma Ltd.

Method

The lyophilised lectin was rehydrated in phosphate buffered saline (PBS; 10 mM $Na_2HPO_4$, 140 mM NaCl, 2.7 mM KCl, 1.8 mM $KH_2PO_4$, pH7.3) to a final concentration of 10 mg/ml. Aliquots of this solution were stored at −20° C. until used.

The lectin was reacted with an equal concentration of SPDP by the addition of a 10 mM stock solution of SPDP in DMSO with mixing. After one hour at room temperature the reaction was terminated by desalting into PBS over a PD-10 column.

The thiopyridone leaving group was removed from the product by reduction with dithiothreitol (DTT, 5 mM, 30 min). The product of this reaction was analysed spectrophotometrically at 280 nm and 343 nm to determine the degree of derivatisation achieved. The degree of derivatisation achieved was 0.8±0.06 mol/mol. The thiopyridone and DTT were removed by once again desalting into PBS over a PD-10 column.

The companion protein was desalted into PBSE (PBS containing 1 mM EDTA). The resulting solution (0.5–1.0 mg/ml) was reacted with a four- or five-fold molar excess of SPDP by addition of a 10 mM stock solution of SPDP in DMSO. After 3 h at room temperature the reaction was terminated by desalting over a PD-10 column into PBS.

A portion of the derivatised companion protein was removed from the solution and reduced with DTT (5 mM, 30 min). This sample was analysed spectrophotometrically at 280 nm and 343 nm to determine the degree of derivatisation. The degree of derivatisation achieved was 2.26±0.10 mol/mol. The bulk of the derivatised companion protein and the derivatised ECL were mixed in proportions such that the ECL was in greater than three-fold molar excess. The conjugation reaction was allowed to proceed for >16 h at 4° C.

The product mixture was centrifuged to clear any precipitate that had developed. The supernatant was concentrated by centrifugation through concentrators (with 10000–50000 molecular weight exclusion limit) prior to a two step purification strategy. As the first step, the concentrated material was applied to a Superose 12 column on an FPLC chromatography system (Pharmacia). The column was eluted with PBS and the elution profile followed at 280 nm.

Figure 1:
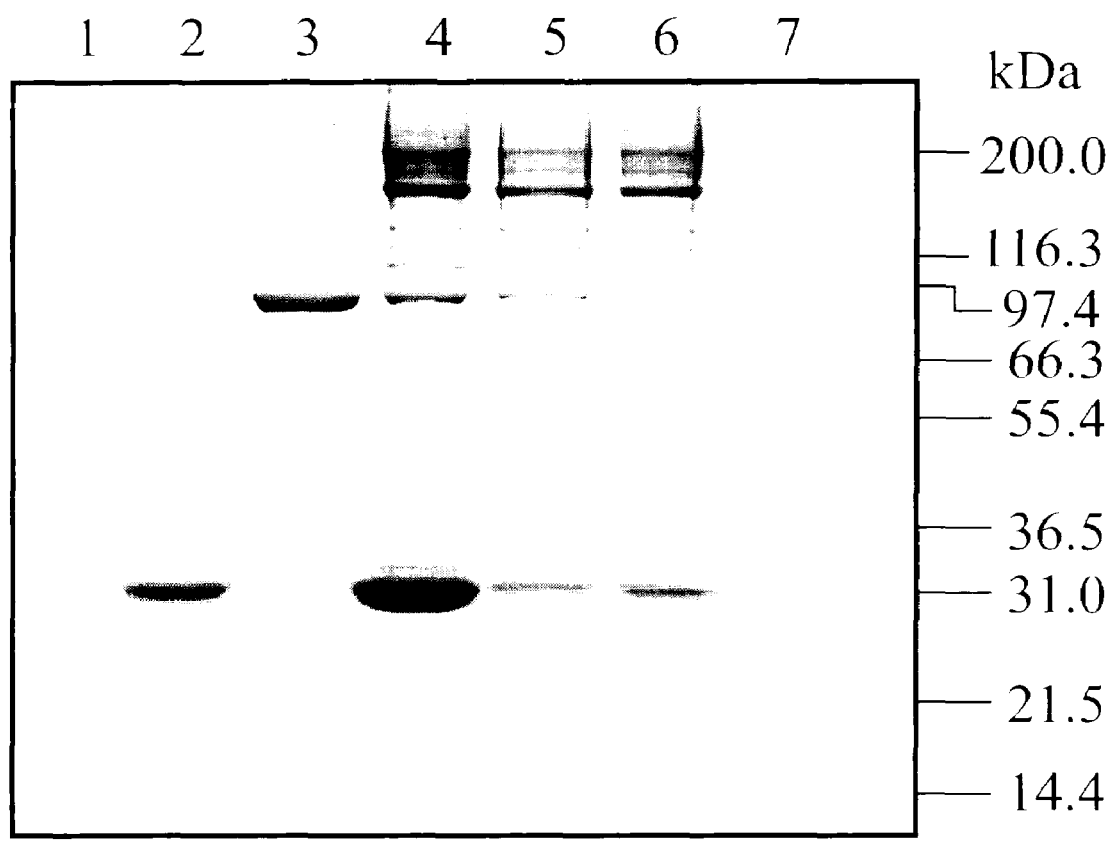
FIG. 1 shows a denaturing polyacrylamide gel analysis of ECL lectin, $LH_N/A$ companion protein and the subsequent chemical conjugates.

Fractions were analysed by SDS-PAGE on 4–20% polyacrylamide gradient gels, followed by staining with Coomassie Blue. The major band of conjugate has an apparent molecular mass of between 130–160 kDa; this is separated from the bulk of the remaining unconjugated companion protein and more completely from the unconjugated ECL. Fractions containing conjugate were pooled prior to the second chromatography step; immobilised lactose-agarose. Selected post-Superose-12 fractions were applied to PBS-washed lactose-agarose and incubated for 2 hours at 4° C. to facilitate binding. Lectin-containing protein conjugates remained bound to the agarose during subsequent washing with PBS to remove contaminants. Lectin conjugate was eluted from the column by the addition of 0.3M lactose (in PBS) and the elution profile followed at 280 nm. The fractions containing conjugate were pooled, dialysed against PBS, and stored at 4° C. until use. FIG. 1 shows a typical SDS-PAGE profile of ECL lectin, companion $LH_N/A$ and the conjugation products at different stages during purification.

EXAMPLE 4

The Production of a Conjugate Between a Lectin from *Erythrina Corallodendron* and a Companion Protein.

The procedure for production of a conjugate between a lectin from *Erythrina corallodendron* and $LH_N/A$ is essentially as described in Example 3 but with the following differences:

Materials

Lectin from *E. corallodendron* (ECorL) was obtained from Sigma Ltd.

EXAMPLE 5

In Vivo Analgesic Effects of *Erythrina Cristagalli* Lectin

Animals

Adult outbred mice (MF1) of either sex, weight range 20 to 30 g have been used for these studies. All animals are acclimatised for a minimum of 4 days by maintaining them in the room in which the tests are to be carried out. Pre-injection data is acquired from all animals on the day before test substances are introduced and this serves as baseline data for individual animals. In addition, this pre-test data allows screening of animals exhibiting extreme responses to the various stimuli. Experiments are done on groups of 10 animals with replicate readings taken at each test point.

Intrathecal Administration.

Mice are anaesthetized by induction with 4% fluothane carried in a 50:50 mixture of oxygen and nitrous oxide with a flow rate of 400–500 cc per minute. Once anaesthesia is induced the percentage is reduced to 1.5 to 2% for maintenance.

The pelvis of the mouse is located, the fur is clipped around the appropriate area and a small incision (about 5 mm) is made in the skin above the spinal column.

Using a 30 gauge disposable needle attached to a 50 μl Hamilton syringe with luer fitting the lectin material is injected into the intrathecal space. The site of injection is normally chosen to be between lumbar vertebrae 5 and 6. Holding the syringe at an angle of about 20° above the vertebral column the needle is inserted into the tissue to one side of the vertebrae so that it slips into the groove between the spinous and transverse processes. The needle is then moved carefully forward to the intervertebral space whilst decreasing the angle of the syringe to about 10°. Once inserted into the appropriate spot a characteristic flick of the tail is often, but not invariably, observed. 5 μl of test material is then injected into the intrathecal space and the needle withdrawn. The skin incision is then closed with a single wound clip and the animal placed in a box to allow recovery. Mice have been observed to recover rapidly from this procedure and become fully mobile within two minutes.

*E. cristagalli* lectin agents were applied intrathecally at 30 μg in a 5 μl volume of physiological saline vehicle. The data in FIG. 2 shows a rapid onset of lectin induced analgesia which approaches a maximum within 1 hour of application and remains constant for at least 5 hours. Lectin induced analgesia is similar to that of a 10 µg/mouse supramaximal (20 times the mouse EC50) of morphine in this test but is of much longer duration; morphine achieves a maximal effect at 1 hour and then declines over a period of 5 hours.

EXAMPLE 6

In Vivo Analgesic Effects of *Erythrina Cristagalli* Lectin Conjugates.

Animals

Adult outbred mice (MF1) of either sex, weight range 20 to 30 g have been used for these studies. All animals are acclimatised for a minimum of 4 days by maintaining them in the room in which the tests are to be carried out. Pre-injection data is acquired from all animals on the day before test substances are introduced and this serves as baseline data for individual animals. In addition, this pre-test data allows screening of animals exhibiting extreme responses to the various stimuli. Experiments are done on groups of 10 animals with replicate readings taken at each test point.

Intrathecal Administration.

Mice are anaesthetized by induction with 4% fluothane carried in a 50:50 mixture of oxygen and nitrous oxide with a flow rate of 400–500 cc per minute. Once anaesthesia is induced the percentage is reduced to 1.5 to 2% for maintenance.

The pelvis of the mouse is located, the fur is clipped around the appropriate area and a small incision (about 5 mm) is made in the skin above the spinal column.

Using a 30 gauge disposable needle attached to a 50 µl Hamilton syringe with luer fitting the lectin material is injected into the intrathecal space. The site of injection is normally chosen to be between lumbar vertebrae 5 and 6. Holding the syringe at an angle of about 20° above the vertebral column the needle is inserted into the tissue to one side of the vertebrae so that it slips into the groove between the spinous and transverse processes. The needle is then moved carefully forward to the intervertebral space whilst decreasing the angle of the syringe to about 10°. Once inserted into the appropriate spot a characteristic flick of the tail is often, but not invariably, observed. 5 µl of test material is then injected into the intrathecal space and the needle withdrawn. The skin incision is then closed with a single wound clip and the animal placed in a box to allow recovery. Mice have been observed to recover rapidly from this procedure and become fully mobile within two minutes.

*E. cristagalli* lectin-$LH_N/A$ conjugates were applied intrathecally at 30 µg in a 5 µl volume of physiological saline vehicle. The data in FIG. 3 shows a rapid onset of lectin-conjugate induced analgesia which approaches a maximum within 1 hour of application and remains constant for at least 5 hours. Lectin-conjugate analgesia is similar in intensity to that of a 10 µg/mouse supramaximal (20 times the mouse EC50) of morphine in this test but is of much longer duration; morphine achieves a maximal effect at 1 hour and then declines over a period of 5 hours.

EXAMPLE 7

In Vivo Analgesic Effects of a Glucosyl-Reactive Lectin from *Triticum Vulgaris*.

Materials

*Triticum vulgaris* wheat germ agglutinin lectin (WGA) was obtained from Sigma Ltd.

Method

Intrathecal administration of *Triticum vulgaris* lectin WGA was as described for Examples 5 and 6.

Figure 4:
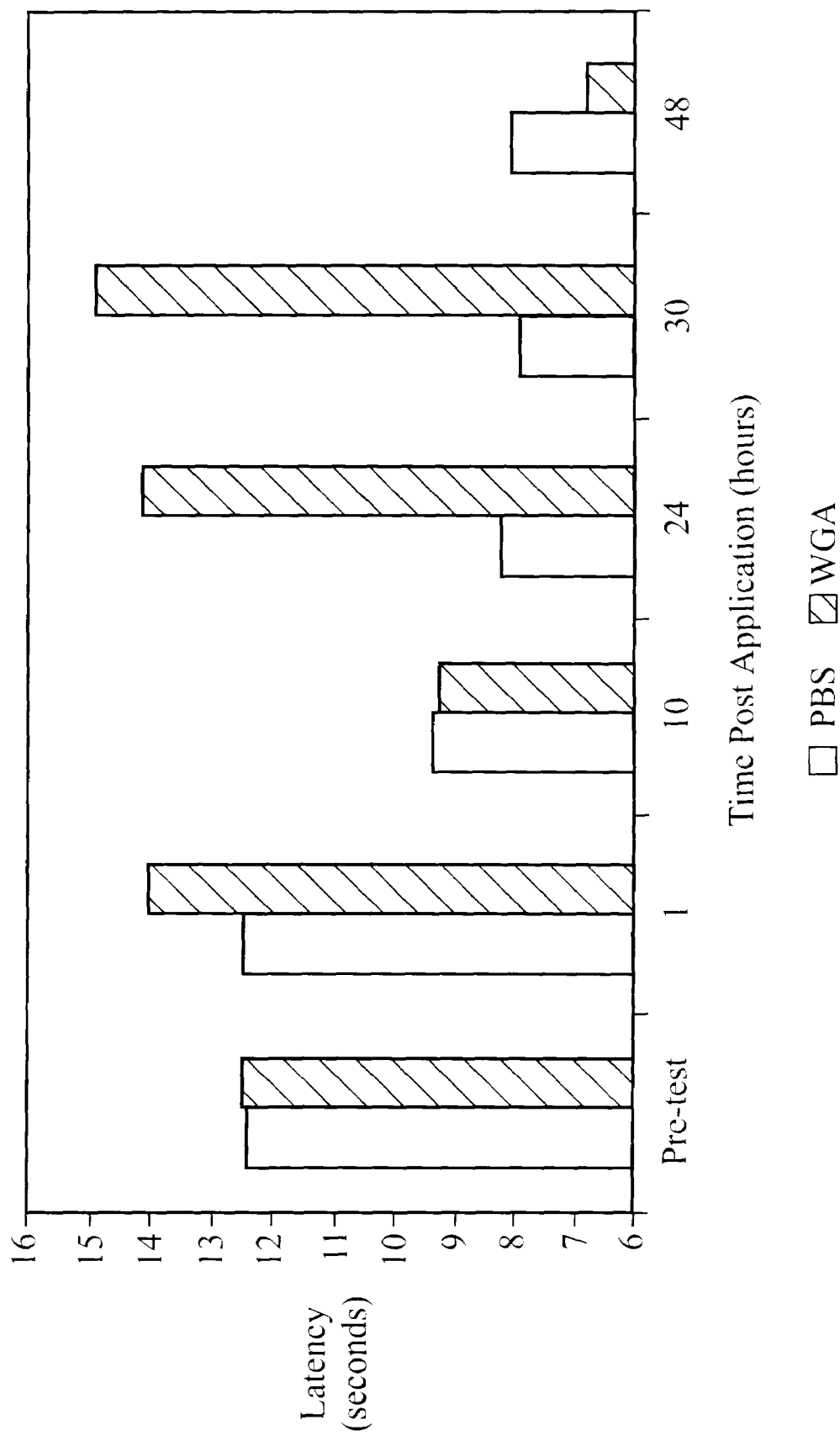
FIG. 4 shows WGA lectin is analgesic in the mouse hot plate model.

The data in FIG. 4 shows that by 24–30 hours post application the hot-plate paw withdrawal time in WGA treated mice is much greater than that of PBS treated control groups. By 48 hours post application the analgesic effect from the single dose has dissipated.

EXAMPLE 8

In Vivo Analgesic Effects of a Galactosyl-Reactive Lectin $IB_4$ from *Bandeiraea Simplicifolia*.

Materials

*Bandeiraea simplicifolia* lectin $IB_4$ was obtained from Sigma Ltd.

Method

Intrathecal administration of *Bandeiraea simplicifolia* lectin $IB_4$ was as described for Examples 5 and 6.

Figure 5:
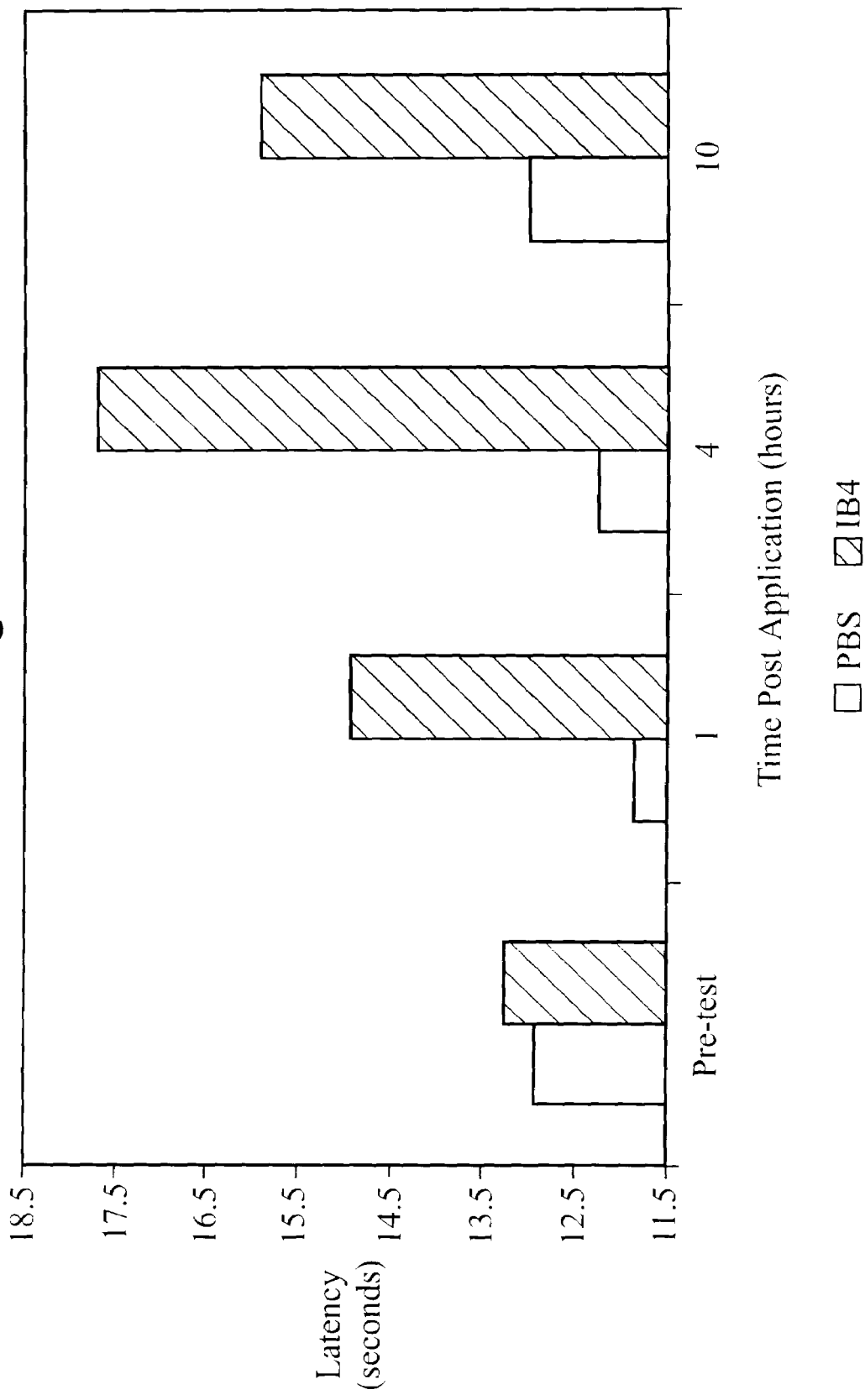
FIG. 5 shows that *Bandeirea simplicifolia* lectin $IB_4$ is analgesic in the mouse hot plate model.

The data in FIG. 5 shows the analgesic effect of a single intrathecal dose of lectin $IB_4$ reagent in a mouse hot plate model over a 10 hour period. A significant increase in withdrawal latency is observed at 1 hour post application with an apparent maximal activity at 4 hours. Analgesia was still clearly discernible over control-group animals at 10 hours post application.

EXAMPLE 9

The Production of a Conjugate Between *Triticum Vulgaris* Lectin and a Companion Protein.

Materials

Lectin from *Triticum vulgaris* (WGA) was obtained from Sigma Ltd. $LH_N/A$ was prepared essentially by the method of Shone C. C., Hambleton, P., and Melling, J. 1987, *Eur. J. Biochem.* 167, 175–180.

SPDP was from Pierce Chemical Co.

PD-10 desalting columns were from Pharmacia.

Dimethylsulphoxide (DMSO) was kept anhydrous by storage over a molecular sieve.

Denaturing sodium dodecylsulphate polyacrylamide gel electrophoresis (SDS-PAGE) and non-denaturing polyacrylamide gel electrophoresis was performed using gels and reagents from Novex.

Additional reagents were obtained from Sigma Ltd.

Method

The lyophilised WGA lectin was rehydrated in phosphate buffered saline (PBS) to a final concentration of 10 mg/ml. Aliquots of this solution were stored at −20° C. until use.

The WGA was reacted with an equal concentration of SPDP by the addition of a 10 mM stock solution of SPDP in DMSO with mixing. After one hour at room temperature the reaction was terminated by desalting into PBS over a PD-10 column.

The thiopyridone leaving group was removed from the product to release a free —SH group by reduction with dithiothreitol (DTT; 5 mM; 30 min). The thiopyridone and DTT were removed by once again desalting into PBS over a PD-10 column.

The companion protein, $LH_N/A$, was desalted into PBSE (PBS containing 1 mM EDTA). The resulting solution (0.5–1.0 mg/ml) was reacted with a four-fold molar excess of SPDP by addition of a 10 mM stock solution of SPDP in DMSO. After 3 h at room temperature the reaction was terminated by desalting over a PD-10 column into PBSE.

A portion of the derivatized $LH_N/A$ was removed from the solution and reduced with DTT (5 mM, 30 min). This sample was analysed spectrophotometrically at 280 nm and 343 nm to determine the degree of derivatisation. The degree of derivatisation achieved was 3.53±0.59 mol/mol.

The bulk of the derivatized $LH_N/A$ and the derivatized WGA were mixed in proportions such that the ExL was in greater than three-fold molar excess. The conjugation reaction was allowed to proceed for >16 h at 4° C.

The product mixture was centrifuged to clear any precipitate that had developed. The supernatant was concentrated by centrifugation through concentrators (with 10000 molecular weight exclusion limit) before application to a Superose 12 column on an FPLC chromatography system (Pharmacia). The column was eluted with PBS and the elution profile followed at 280 nm.

Fractions were analysed by SDS-PAGE on 4–20% polyacrylamide gradient gels, followed by staining with Coomassie Blue (FIG. 6). The major conjugate products have an apparent molecular mass of between 106–150 kDa, these are separated from the bulk of the remaining unconjugated $LH_N/A$ and more completely from the unconjugated WGA.

Fractions containing conjugate were pooled prior to addition to PBS-washed N-acetylglucosamine-agarose. Lectin-containing proteins (ie. WGA-$LH_N/A$ conjugate) remained bound to the agarose during washing with PBS to remove contaminants (predominantly unconjugated $LH_N/A$). WGA-$LH_N/A$ conjugate was eluted from the column by the addition of 0.3M N-acetylglucosamine (in PBS) and the elution profile followed at 280 nm.

The fractions containing conjugate were pooled, dialysed against PBS, and stored at 4° C. until use.

On the gel there are bands due to lectin alone in fractions containing the conjugate, this material is probably due to the non-covalent homo-dimeric nature of the WGA; where only one monomer of WGA is covalently attached to the $LH_N/A$ the other is dissociated from the complex by the SDS in the electrophoretic procedure giving rise to these bands.

EXAMPLE 10

The Production of a Conjugate Between *Erythrina Corallodendron* Lectin and a Companion Protein.

Materials

*Erythrina corallodendron* lectin was obtained from Sigma.

Method

The methodology for production of *Erythrina corallodendron* lectin conjugated to a companion protein is similar to that described in Example 9 for the production of WGA-$LH_N/A$. See FIG. 7 for SDS-PAGE analysis of conjugated protein.

EXAMPLE 11

The Production of a Conjugate Between *Bandeiraea Simplicifolia* Lectin and a Companion Protein.

Materials

*Bandeiraea simplicifolia* lectin was obtained from Sigma.

Method

The methodology for production of *Bandeiraea simplicifolia* lectin conjugated to a companion protein is similar to that described in Example 9 for the production of WGA-$LH_N/A$. See FIG. 8 for SDS-PAGE analysis of conjugated protein.

EXAMPLE 12

Preparation of Oligomeric *Erythrina Cristagalli* Lectin.

Materials

*Erythrina cristagalli* lectin was obtained from Sigma.
SPDP & SMPB were obtained from Pierce.

Method

The lyophilised lectin was rehydrated in phosphate buffered saline (PBS) to a final concentration of 2 mg/ml.

An aliquot of ECL was reacted with a 1.5 times molar excess of SPDP by the addition of a 10 mM stock solution of SPDP in DMSO. After rotating for 90 minutes at room temperature, the reaction was terminated by desalting into PBS over a PD-10 column.

The thiopyridone leaving group was removed from the product to release a free —SH group by reduction with dithiothreitol (DTT; 5 mM; 30 min). The thiopyridone and DTT were removed by once again desalting into PBS over a PD-10 column.

A second aliquot of ECL was reacted with a 2.5 times molar excess of SMPB (a non-reducible linker) by the addition of a 10 mM stock solution of SMPB in DMSO. After rotating for 90 minutes at room temperature, the reaction was terminated by desalting into PBS over a PD-10 column.

The derivatised ECL samples were mixed together and the conjugation reaction was allowed to proceed by rotation at 4° C. for >16 h.

Aliquots of the derivatised lectins and the product mixture were analysed by SDS-PAGE on 4–20% polyacrylamide gradient gels, followed by staining with Coomassie Blue (see FIG. 9).

EXAMPLE 13

Preparation of Recombinant *Erythrina Cristagalli* Lectin.

Materials

Viable *Erythrina cristagalli* seeds were obtained from a local horticultural distributor.

Method

A number of methods for obtaining the coding sequence for *Erythrina cristagalli* lectin (ECL) were employed. In the first instance, methodology similar to that described by Arango et al for *Erythrina corallodendron* [Arango, R., Rozenblatt, S, & Sharon, N. (1990), FEBS Lett. 264, 109–111] was used to isolate the coding sequence from messenger RNA.

Alternatively, the coding sequence for *Erythrina cristagalli* was obtained by specific amplification from genomic DNA. Briefly, genomic DNA was extracted from *Erythrina cristagalli* using commercially sourced DNA extraction kits. The sequence of the N-terminal amino acids of ECL was determined in order to facilitate primer design. Using degenerate primers designed to have homology with the N-terminus of ECL and the published sequence of *Erythrina corallodendron*, amplification of coding region was facilitated.

Specific amplification product was isolated, cloned into a suitable vector and sequenced. Sequence data confirmed the presence of codons suitable for the expression of polypeptide that had homology to the lectin isolated from *Erythrina corallodendron*.

ECL coding region was cloned into a suitable expression vector and expression of recombinant ECL induced. Recombinant ECL was observed by Western blotting using antisera raised against native ECL.

EXAMPLE 14

In Vitro Modulation of C-Fibre Activity by *Erythrina Cristagalli* Lectin.

Materials

Substance P EIA kit was obtained from Cayman Chemical Company (690 KMS Place, Ann Harbor, Mich. 48108, USA).

Method

Embryonic DRG were prepared according to Welch et al [Welch M J, Foster K A. (1999) Embryonic rat spinal sensory ganglia. In: The Neuron in Tissue Culture (Haynes L W, ed), John Wiley and Sons. *IBRO Handbook Series: Methods in the Neurosciences* 18 389–392].

Material was applied between seven and fourteen days post initiation of culture and incubated for 3 days prior to assay. After washing with HBSS-D the substance P release capability of the cells was determined by the following method. Wells were washed twice with low potassium buffer (5 mM KCl, 144 mM NaCl, 1 mM $MgCl_2$, 0.4 mM glucose, 10 mM HEPES (pH 7.4), 2 mM $CaCl_2$).

Basal samples were then obtained by incubating each well for 5 minutes with 1 ml low potassium buffer. Following removal of basal samples cells were stimulated by incubating with 1 ml high potassium buffer (40–120 mM KCl isotonically balanced with NaCl) for five minutes.

Substance P immunoreactivity was measured using the Substance P Enzyme Immunoassay Kit manufactured by Cayman Chemical Company (690 KMS Place, Ann Harbor, Mich. 48108, USA) according to manufacturers' instructions and is expressed in pg/ml relative to a standard substance P curve run in parallel.

*Erythrina cristagalli* lectin was demonstrated to modulate the release of substance P in a dose-dependent manner (see FIG. 10). At low doses, release of substance P is slightly enhanced above control release, whereas at high concentrations release of substance P is clearly inhibited. This indicates that *Erythrina cristagalli* lectin is able to modulate the activity of C-fibres by preventing release of a key neurotransmitter.

EXAMPLE 15

In Vitro Modulation of C-Fibre Activity by *Erythrina Cristagalli* Lectin-Protein Conjugates Materials & Method The preparation of dorsal root ganglia (eDRG) and assay of substance P release were as described previously.

A lectin-protein conjugate of the type described in Example 17 was applied to eDRG and substance P release assessed. FIG. 11 is representative of such an experiment and demonstrates that *Erythrina cristagalli* lectin conjugated to another protein is capable of modulating release of substance P from an in vitro model of C-fibres.

EXAMPLE 16

In Vivo Modulation of C-Fibre Activity by *Erythrina Cristagalli* Lectin.

Method

Electrophysiological studies of C-fibre activity were conducted in anaesthetized Sprague-Dawley rats essentially as described by Diaz, A. and Dickenson, A. H. 1997 *Pain*. 69, 93–100.

Briefly, anaesthesia was induced with 2–3% halothane in 66% $N_2O$—33% $O_2$ and a tracheal cannula was inserted. Rats were placed in a stereotaxic frame and a laminectomy performed to expose segments L4–L5 of the spinal cord. Clamps caudal and rostral to exposed section held the cord rigid and the animals spontaneously breathed while maintained in a state of areflexia with 1.5–1.8% halothane.

Extracellular recordings of convergent dorsal horn neurons were made with parylene coated tungsten electrodes which were lowered into the spinal cord by a SCAT (Digitimer) microdrive to a mean depth of 700 μm, corresponding to the main zone of output cells from the cord to the brain.

Data were captured and then analysed by Spike 2 software. Selected neurons had a clear short latency (0–20 ms) Aβ-fibre evoked response followed by Aδ-fibre response and then C-fibre evoked response (90–300 ms) after transcutaneous electrical stimulation (2 ms wide pulses at a frequency of 0.5 Hz) of the centre of the receptive field. Trains of sixteen stimuli allowed construction of post stimulus histograms. Any neuronal responses occurring 300–800 ms post-stimulus were taken as the post-discharge/afterdischarge of hyperexcitable neurons.

Figure 12:
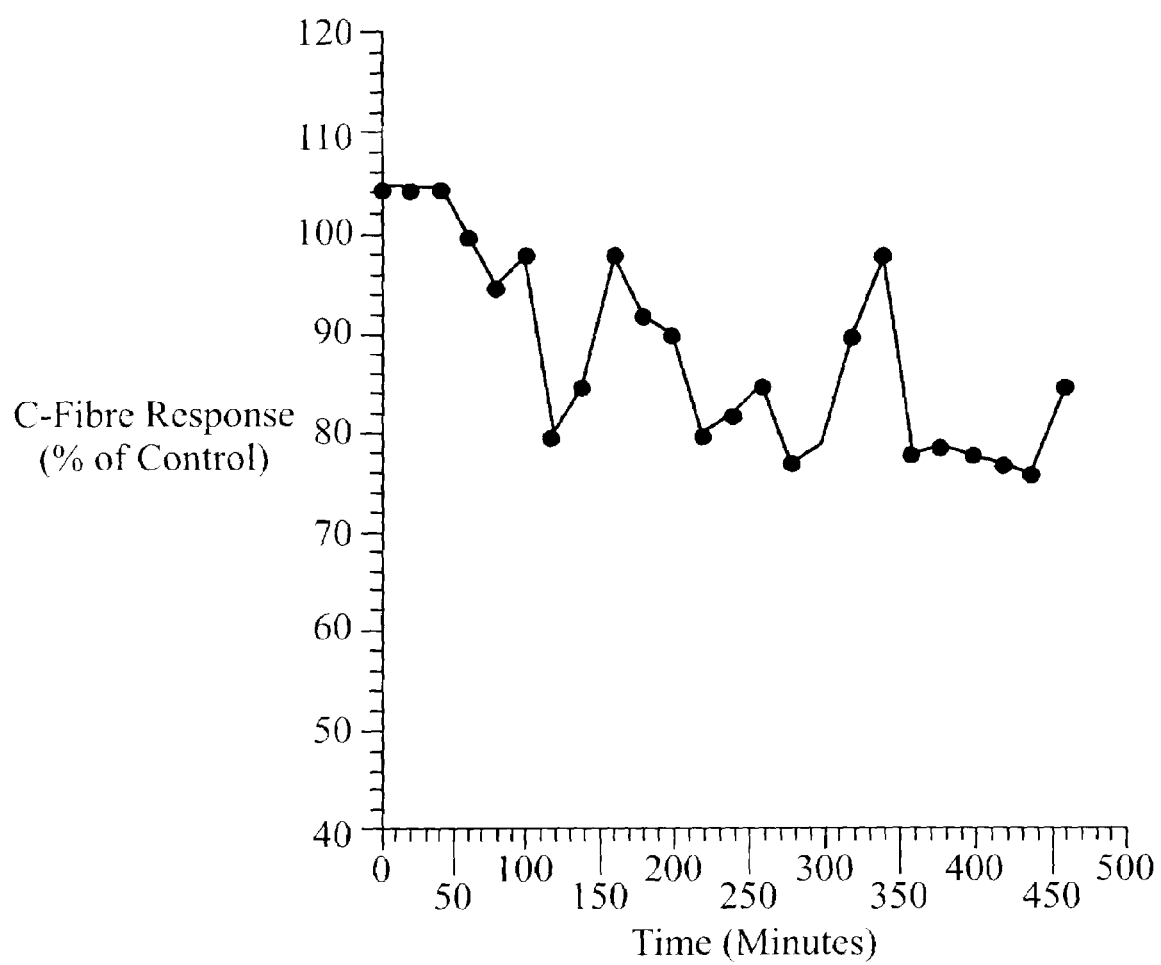
FIG. 12 illustrates inhibition of C-fibre response to stimulation by *Erythrina cristagalli* lectin.

230 μg lectin from *Erythrina cristagalli* was applied in 50 μl and C-fibre activity observed. FIG. 12 is illustrative of data obtained from such an approach and demonstrates the downward trend of C-fibre response, compared to controls, over the time of the experiment.

EXAMPLE 17

In Vivo Analgesic Effects of *Erythrina Cristagalli*-$LH_N$/A (–) Conjugates

Materials

Using site-directed mutagenesis, a mutant of $LH_N$/A ($LH_N$/A(–)) was prepared that possessed a tyrosine residue at position 227 in place of the native histidine. This mutant is know in the art to result in a protein that is defective in its endopeptidase activity [Zhou, L., de Pavia, A., Liu, D., Aoki, R. & Dolly, J. O., 1995, Biochemistry, 34, 15175].

$LH_N$/A(–) was conjugated to a lectin from *Erythrina cristagalli* according to the method described in Example 11.

Methods

Intrathecal administration of *Erythrina cristagalli*-$LH_N$A (–) conjugate was as described in Examples 5, 6 and 19.

EXAMPLE 18

In Vivo Modulation of Antidromic C-Fibre Activity by *Erythrina Cristagalli* Lectin.

Materials & Method

The effect on antidromic C-fibre activity in response to application of *Erythrina cristagalli* was assessed in vivo following similar methodology to that reported by Pinter et al [Pinter, E., Brown, B., Hoult, J. R. S. & Brain, S. D. (1999) European Journal of Pharmacology, 369, 91–98], Lambeck & Holzer [Lembeck, F. & Holzer, P. (1979) *Naunyn-Schmiedeberg's Arch. Pharmacol.*, 310, 175–183] and Garret et al [Garret, C., Carruette, A., Fardin, V., Moussaoui, S., Peyronel, J.-F., Blanchard, J-C and Laduron, P. M. (1991) Proc. Natl. Acad. Sci., 88, 10208–10212].

*Erythrina cristagalli* was demonstrated to reduce extravasation induced by antidromic C-fibre activity (see FIG. 13).

The neurogenic inflammatory response occurs as a result of neuropeptide release from the endings of stimulated primary afferent neurones. The major neuropeptides involved are considered to be substance P, which acts to increase microvascular permeability, so allowing the exudation of plasma proteins from the blood vessels into the tissues, and CGRP, which is a potent vasodilator, and potentiates the oedema response to substance P. These combined phenomena result in inflammatory oedema formation. Furthermore, neurogenic inflammation is thought to be a component of several disorders and diseases, ranging from sunburn and psoriasis in the skin, to migraine, asthma, and rheumatoid arthritis. This study investigated the ability of *Erythrina cristagalli* to modulate neurogenic inflammation induced by electrical stimulation.

All experiments were carried out in accordance with the Animals (Scientific Procedures) Act 1986.

Neurogenic oedema formation in the rat hind paw *Erythrina cristagalli* was administered 4 hr before the start of oedema measurements. Anaesthesia was induced and maintained by isoflurane. *Erythrina cristagalli* (1 mg in 100 Fl Tyrode's solution) was injected i.d into the innervated paw skin in two rats and Tyrode (vehicle control) injected similarly into two separate rats.

The rats were allowed to recover then left for 4 hr before oedema measurements were carried out. Rats were anaesthetized for the terminal protocol by intraperitoneal injection of sodium pentobarbitone (Sagatal 60 mg kg$^{-1}$). The tail vein was cannulated to allow the maintenance of anaesthesia with sodium pentobarbiton (15 mg ml$^{-1}$ i.v. as required). The ipsilateral hind limb was shaved and the saphenous nerve dissected clear of surrounding tissue. The nerves were then ligated centrally and immersed in mineral oil for the duration of the experiment. Rats were placed on an automatic heating pad to maintain the body temperature at 36–38° C.

The animals were left for about 20 min to allow a stabilisation period after dissection. The animals then received $^{125}$I-bovine serum albumin (180 kBq) and Evans Blue dye (0.2–0.5 ml of 2.5% w/v in saline) i.v. via the tail vein in order to visualize and quantify plasma extravasation in paw skin. The saphenous nerve was then carefully, without pulling, lifted onto a platinum electrode. The nerve was then stimulated (10 V, 1 ms, 2 Hz, 5 min) and plasma was allowed to accumulate for 0–30 min. At the end of the accumulation period, a blood sample was taken by cardiac puncture and centrifuged at 6000 g for 4 min to obtain a plasma sample.

The animal was killed by anaesthetic overdose and cervical dislocation and the skin of the innervated areas of both hind paws was removed and weighed. The gamma emissions from plasma and skin were measured in a multi-channel counter (Wallac, UK) and microvascular extravasation was calculated by comparison to a known volume of blood plasma. The plasma extravasated was calculated and expressed as the volume of plasma per 100 mg tissue for the stimulated and control untreated leg.

The results are shown in FIG. 13. Oedema formation induced via this protocol in previous experiments is normally observed as approximately 30 μl plasma/100 mg tissue. It can be observed that the rat treated with vehicle produced the expected response. Both paws treated with *Erythrina cristagalli*, produced what may be described as a trend towards an inhibitory effect.

Thus *Erythrina cristagalli* modified neurogenic inflammation induced following electrically-mediated neuropeptide release.

EXAMPLE 19

In Vivo Modulation of C-Fibre Activity by *Erythrina Cristagalli* Lectin.

Animals

Adult outbred mice (MF1) of either sex, weight range 20 to 30 g have been used for these studies.

All animals were acclimatised by maintaining them in the room in which the tests are to be carried out for a minimum of 4 days.

Materials & Method

Test and control substances were administered by the intrathecal route using the following procedure. Mice are anaesthetized by induction with 4% fluothane carried in a 50:50 mixture of oxygen and nitrous oxide with a flow rate of 400–500 cc per minute.

Once anaesthesia is induced the percentage is reduced to 1.5 to 2% for maintenance. The pelvis of the mouse is located, the fur is clipped around the appropriate area and a small incision (about 5 mm) is made in the skin above the spinal column.

Test material is injected into the intrathecal space using a 30 gauge disposable needle attached to a 50 μl Hamilton syringe with luer fitting. The site of injection was normally chosen to be between lumbar vertebrae 1 and 3. Holding the syringe at an angle of about 20° above the vertebral column the needle is inserted into the tissue to one side of the vertebrae so that it slips into the groove between the spinous and transverse processes. The needle is then moved carefully forward to the intervertebral space whilst decreasing the angle of the syringe to about 10°.

Once inserted into the appropriate spot a characteristic flick of the tail is often, but not invariably, observed. 5 μl of test material is then injected into the intrathecal space and the needle withdrawn. The skin incision is then closed with a single wound clip and the animal placed in a box to allow recovery.

Mice have been observed to recover rapidly from this procedure and become fully mobile within two minutes.

Pre-injection data was acquired from all animals on the day before test substances are introduced. This pre-test data allows screening of animals exhibiting extreme responses to the various stimuli and allocation to groups such that the mean group latency was equivalent. Response to thermal stimuli (hot plate) was determined 20 hours post injection of test and control substances.

Hot Plate

The equipment is switched on to equilibrate for 15 minutes before tests commence. The temperature is normally set at 55° C. Individual animals are placed on the surface of the hotplate and observed closely and the time noted when one hind paw is deliberately withdrawn from the surface.

At this point the animal is immediately removed from the apparatus. In order to prevent tissue damage due to profound analgesia a maximum duration of 30 seconds is allowed for this test.

FIG. 14 illustrates data obtained following application of a range of concentrations of *Erythrina cristagalli* lectin to the spinal cord. Response to thermal stimuli is modified in a dose-dependent manner, indicative of C-fibre modulation.

The invention claimed is:

1. A method of treating pain resulting from C-fibre neuron activity, comprising administering to a patient a lectin in an amount effective to inhibit C-fibre neuron activity, wherein the lectin is an *Erythrina cristagalli* lectin.

2. A method of treating pain resulting from C-fibre neuron activity, comprising administering to a patient a lectin in an amount effective to inhibit C-fibre neuron activity, wherein the lectin is *Bandeiraea simplicifolia* lectin $IB_4$.

3. A method of treating pain resulting from C-fibre neuron activity, comprising administering to a patient a lectin in an amount effective to inhibit C-fibre neuron activity, wherein the lectin is *Triticum vulgaris* wheat germ agglutinin lectin (WGA).

4. A method of treating inflammation resulting from C-fibre neuron activity, comprising administering to a patient a lectin in an amount effective to inhibit C-fibre neuron activity, wherein the lectin is an *Erythrina cristagalli* lectin.

* * * * *